US009017663B2

(12) United States Patent
Al-Atari Abou-Asi et al.

(10) Patent No.: US 9,017,663 B2
(45) Date of Patent: Apr. 28, 2015

(54) PLURIPOTENT STEM CELLS OBTAINED FROM DENTAL PULP

(75) Inventors: Maher Al-Atari Abou-Asi, Barcelona (ES); Núria Casals Farré, Castelldefels (ES); Lluís Giner Tarrida, Cerdanyola del Vallés (ES); Eduardo Ferrés Padró, Barcelona (ES)

(73) Assignee: Universitat Internacional de Catalunya, Barcelona (ES)

(*) Notice: Subject to any disclaimer, the term of this patent is extended or adjusted under 35 U.S.C. 154(b) by 0 days.

(21) Appl. No.: 13/386,324

(22) PCT Filed: Jul. 21, 2010

(86) PCT No.: PCT/EP2010/060539
§ 371 (c)(1),
(2), (4) Date: Jan. 31, 2012

(87) PCT Pub. No.: WO2011/009878
PCT Pub. Date: Jan. 27, 2011

(65) Prior Publication Data
US 2012/0251504 A1  Oct. 4, 2012

(30) Foreign Application Priority Data
Jul. 21, 2009 (ES) .................................. 200930488

(51) Int. Cl.
C12N 5/071 (2010.01)
C12N 5/074 (2010.01)
C12N 5/0775 (2010.01)

(52) U.S. Cl.
CPC ............ *C12N 5/0607* (2013.01); *C12N 5/0664* (2013.01); *C12N 2500/25* (2013.01); *C12N 2501/135* (2013.01); *C12N 2501/235* (2013.01)

(58) Field of Classification Search
USPC ................................................ 435/366, 325
See application file for complete search history.

(56) References Cited

U.S. PATENT DOCUMENTS

2008/0152629 A1  6/2008  Edinger et al.

FOREIGN PATENT DOCUMENTS

| WO | WO 2005/001076 A2 | 1/2005 |
| WO | WO 2006/088867 | 8/2006 |
| WO | WO 2008/080200 A1 | 7/2008 |
| WO | WO 2009/072527 | 6/2009 |
| WO | WO 2009/156495 | 12/2009 |

OTHER PUBLICATIONS

Kerkis et al., Isolation and characterization of a population of immature dental pulp stem cells expressing OCT-4 and other embryonic stem cell markers. Cells Tissues Organs, vol. 184 (2006) pp. 105-116.*
Kerkis et al., Stem cells in dental pulp of deciduous teeth. Tissue Engineering Part B: Reviews, vol. 18 No. 2 (2012) pp. 129-138.*
Liu et al., Dental pulp stem cells. Methods in Enzymology, vol. 419 (2006) pp. 99-113.*
Atari et al., Dental Pulp of the third molar: a new source of pluripotent-like stem cells. Journal of Cell Science, vol. 125 (2012) pp. 3343-3356.*
Prelle et al., "Establishment of Pluripotent Cell Lines from Vertebrate Species—Present Status and Future Prospects," Cells Tissues Organs, 165:220-236 (1999).
Niwa et al., "Quantitative expression of Oct-3/4 defines differentiation, dedifferentiation or self-renewal of ES cells," Nature Genetics, vol. 24, pp. 372-376 (2000).
Venable et al., "Lectin binding profiles of SSEA-4 enriched, pluripotent human embryonic stem cell surfaces," BMC Developmental Biology, 5:15 (2005).
Young et al., "Human Pluripotent and Progenitor Cells Display Cell Surface Cluster Differentiation Markers CD10, CD13, CD56, and MHC Class-I," Proceedings of the Society for Experimental Biology and Medicine, 221:63-72 (1999).
Jiang et al., "Pluripotency of mesenchymal stem cells derived from adult marrow," Nature, vol. 418, pp. 41-49 (2002).
Koyama et al., "Evaluation of Pluripotency in Human Dental Pulp Cells," J. Oral Maxillofac. Surg., 67: 501-506 (2009).
Gronthos et al., "Postnatal human dental pulp stem cells (DPSCs) in vitro and in vivo," PNAS, vol. 97, No. 25, pp. 13625-13630 (2000).
Kerkis et al., "Isolation and Characterization of a Population of Immature Dental Pulp Stem Cells Expressing OGT-4 and Other Embryonic Stem Cell Markers," Cell Tissues Organs, 184:105-116 (2006).
Todorov et al., "Multipotent Progenitor Cells Isolated from Adult Human Pancreatic Tissue," Transplantation Proceedings, 37, 3420-3421 (2005).
Smith et al., "Inhibition of pluripotential embryonic stem cell differentiation by purified polypeptides," Nature, vol. 336, pp. 688-690 (1988).
Haynesworth et al., "Characterization of cells with osteogenic potential from human marrow," Bone, vol. 13, Issue 1, pp. 81-88 (1992).
Jiang et al., "Multipotent adult progenitor cells from human bone marrow differentiate into hepatocyte-like cells induced by co-culture with human hepatocyte line," National Medical Journal of China, vol. 87, No. 6, pp. 414-418 (2007).
Jiang et al., "Multipotent progenitor cells can be isolated from postnatal murine bone marrow, muscle, and brain," Experimental Hematology, vol. 30, Issue 8, pp. 896-904 (2002).
Bosello et al., "Baff and rheumatic autoimmune disorders: implications for disease management and therapy," International Journal of Immunopathology and Pharmacology, vol. 20, No. 1, pp. 1-8 (2006).
Chen et al., "Establishment of a pluripotent embryonic cell line from sea perch (*Lateolabrax japonicus*) embryos," Aquaculture, vol. 218, pp. 141-151 (2003).

(Continued)

*Primary Examiner* — Jon P Weber
*Assistant Examiner* — Kara Johnson
(74) *Attorney, Agent, or Firm* — Squire Patton Boggs (US) LLP

(57) ABSTRACT

The present invention relates to pluripotent stem cells obtained from the dental pulp of patients of different ages, the invention furthermore comprises cultures of said cells, means for obtaining them and pharmaceutical compositions comprising them, as well as their application in tissue regeneration.

5 Claims, 17 Drawing Sheets

(56) References Cited

OTHER PUBLICATIONS

Morsczeck et al., "The state of the art in human dental stem cell research," Mund Kiefer GesichtsChir., 11:259-266 (2007).

Sloan et al., "Stem cells and the dental pulp: potential roles in dentine regeneration and repair," Oral Diseases, 13:151-157 (2007).

Atari et al., "Dental Pulp of the Third Mollar: A New Source of Pluripotent-like Stem Cells", *J Cell Sci* (2012) 125:3343-3356.

Beltrão-Braga et al., "Feeder-Free Derivation of Induced Pluripotent Stem Cells From Human Immature Dental Pulp Stem Cells", *Cell Transplantation* (2011) 20:1707-1719.

Kerkis et al., "Stem Cells in Dental Pulp of Deciduous Teeth", *Tissue Engineering: Part B* (2012) 18:129-138.

Gronthos et al., Postnatal human dental pulp stem cells (DPSCs) in vitro and in vivo, PNAS (2000) 97:13625-13630.

Ballini et al., "In Vitro Stem Cell Cultures from Human Dental Pulp and Periodontal Ligament: New Prospects in Dentistry," International Journal of Immunopathology and Pharmacology, vol. 20, No. 1, pp. 9-16 (2007).

Barry et al., "The SH-3 and SH-4 Antibodies Recognize Distinct Epitopes on CD73 from Human Mesenchymal Stem Cells," Biochemical and Biophysical Research Communications, vol. 289, pp. 519-524 (2001).

Gronthos et al., "Stem Cell Properties of Human Dental Pulp Stem Cells," Journal of Dental Research, vol. 81, No. 8, pp. 531-535 (2002).

Ikeda et al., "Multipotent cells from the human third molar: feasibility of cell-based therapy for liver disease," Differentiation 76, pp. 495-505 (2008).

Liu et al., "One-Step Derivation of Mesenchymal Stem Cell (MSC)-Like Cells from Human Pluripotent Stem Cells on a Fibrillar Collagen Coating," PLoS One vol. 7, issue 3, e33225, 9 pgs. (2012).

Ulloa-Montoya et al., "Culture Systems for Pluripotent Stem Cells," J. of Biosci. & Bioengineering vol. 100, No. 1, pp. 12-27 (2005).

Rius et al., "Reliability of short comparative genomic hybridization in fibroblasts and blastomeres for a comprehensive aneuploidy screening: first clinical application," Human Reproduction vol. 25, No. 7, pp. 1824-1835 (2010).

Villa-Diaz et al., "Derivation of Mesenchymal Stem Cells from Human Induced Pluripotent Stem Cells Cultured on Synthetic Substrates," Stem Cells vol. 30, pp. 1174-1181 (2012).

\* cited by examiner

PLURIPOTENT STEM CELLS OBTAINED FROM DENTAL PULP

This application is the National Stage of International Application No. PCT/EP2010/060539, filed Jul. 21, 2010, which claims the benefit of Spanish Application No. ES P 200930488, filed Jul. 21, 2009, and U.S. Provisional Application No. 61/249,846, filed Oct. 8, 2009, each of which is incorporated by reference in its entirety.

The present invention relates to pluripotent stem cells obtained from the dental pulp of patients of different ages and their application in tissue regeneration.

BACKGROUND ART

In living beings, tissues suffer from wear throughout life but they have a self-renewal capacity. If this renewal did not exist, the life expectancy of living beings would be considerably reduced. Specifically, stem cells are the ones which have this tissue self-renewal capacity. The self-renewal capacity is shown by the capacity to produce more stem cells and, in addition, to generate cells of one or more differentiated cell types.

The replicative decrease of stem cells involves the degeneration and death of the different tissues, either in an acute manner (infarctions) or in a chronic manner (degeneration-aging).

Due to the mentioned self-renewal capacity, cell therapy with stem cells is currently applied, among others, in: heart pathologies, corneal pathologies and pelvic floor pathologies. Fistulas, especially in patients with Crohn's disease, are also treated.

Stem cells can be classified according to their differentiation potential as: totipotent, pluripotent and multipotent.

Totipotent stem cells can grow and form a complete organism, forming both embryonic components (such as the three germ layers, the germline and the tissues which will give rise to the yolk sac, for example) and extraembryonic components (such as the placenta). In other words, they can form all the cell types.

Multipotent stem cells are those which can only generate cells of their own germ layer or germline of origin, for example: since a bone marrow mesenchymal stem cell has a mesodermal nature, it will give rise to cells of that layer such as myocytes, adipocytes or osteocytes, among others.

Pluripotent stem cells cannot form a complete organism, but they can differentiate into cells from the three germ layers: (a) ectoderm, which is the origin of the nervous system, the respiratory system, upper digestive tract (stomodeum), the epidermis and its adnexa (hair and nails) and the mammary glands; (b) endoderm, which is the origin of the intestine, the liver, the pancreas, the lungs and most of the internal organs; and (c) mesoderm, which is the origin of the skeletal system, the muscles and the circulatory and reproductive systems. They can also form any other type of cell from the germ and the yolk sac.

The fact that pluripotent cells have the capacity to differentiate into such a large number of tissues makes them especially interesting for the design of new therapies in general and of regenerative therapies in particular. Currently, pluripotent stem cells in adult individuals are mainly obtained from bone marrow.

It is well known in the state of the art that when pluripotent stem cells are isolated and characterized from the extracted bone marrow sample, there are different well-established criteria in the state of the art which allow clearly classifying a stem cell as a pluripotent cell.

A first criterion would be to determine the capacity of the isolated cell to differentiate into tissues derived from the three germ layers (endoderm, ectoderm and mesoderm) using commercially available differentiation media (Prelle et al., "Establishment of pluripotent cell lines from vertebrate species, present status and future prospects", Cell Tissues Organs, 1999, vol. 165, pp. 220-236).

A second criterion would consist of identifying the markers expressed by the isolated stem cell. For example, the expression of the gene OCT3/4 has been described as necessary for a stem cell to be pluripotent, Niwa et al. "Quantitative expression of Oct-3/4 defines differentiation, dedifferentiation or self-renewal of ES cells", Nature, 2000 vol. 24, pp. 372-376. The expression of SSEA4 in pluripotent cells has been described by Venable et al. "Lectin binding profiles of SSEA-4 enriched, pluripotent human embryonic stem cell surfaces" BMC Dev Biol. 2005, vol. 21, pp. 5-15, and the expression of CD13 also in pluripotent cells is mentioned in the publication of Young et al., "Human pluripotent and progenitor cells display cell surface cluster differentiation markers cd10, cd13, cd56, and mhc class-I", Proceedings of the Society for Experimental Biology and Medicine, 1999 vol. 221, no. 1, pp. 63-7.

Jiang et al. (cf. Jiang et al. "Pluripotency of mesenchymal stem cells derived from adult marrow", Nature, 2002, vol. 418, pp. 41-47) have described the characterization of pluripotent stem cells in a cell population of the bone marrow. This population is the so-called MAPCs (multipotent adult progenitor cells). This article indicates that MAPCs express high levels of CD13, SSEA-4 and OCT3/4, typical pluripotent cell markers. Like embryonic stem cells, in MAPCs the activation of the transcription factors OCT-4, NANOG and REX-1 is detected, which factors are necessary for maintaining the cell in a proliferative and undifferentiated state. Cloning assays which demonstrate that it is a single cell which is capable of differentiating into tissues of any of the three germ layers (endoderm, mesoderm or ectoderm) are additionally included. The source of pluripotent stem cells described in this article is bone marrow. A general or local anesthesia is necessary in the extractions of stem cells from bone marrow. The method which is used to obtain them is aspirating the marrow content by means of the puncture of a bone. The material which is obtained passes through a series of screening processes to separate the cells. This makes obtaining these cells a complex and inefficient process.

Due to the foregoing, it is necessary to find alternative sources from which pluripotent stem cells can be extracted.

SUMMARY OF THE INVENTION

The researchers of the present invention have discovered that dental pulp is a source of pluripotent stem cells, hereinafter also referred to as "DPPSCs".

Advantageously, the cells of the invention are always present in humans, regardless of their age, although the proportion decreases. As illustrated below, the stem cells obtained from this tissue preferably express the markers CD13, SSEA4 OCT3/4 and CD105, which indicates that said cells are of the pluripotent type.

It has furthermore been proved that since the stem cells isolated from dental pulp are pluripotent, they have the capacity to differentiate into tissues from each of the three germ layers. This makes them interesting in the field of surgery, and particularly in the field of the reconstruction of tissues, such as bone, neuronal and liver tissue.

Thus, the present invention relates in a first aspect to a pluripotent stem cell characterized in that it is obtained from dental pulp and expresses at least the genes NANOG, SOX2, and expresses the markers SSEA4, OCT3/4 and CD105. According to the present invention, the terms gene and marker referred in claim 1 can be used interchangeably.

The cells of the invention have a small size between 5 and 8 microns. Furthermore, they do not present chromosome abnormalities or structural changes during culture, which are important aspects for their use in cell therapy for tissue regeneration.

In addition, the cells of the invention are adult pluripotent stem cells. The fact that they are adult confers the advantages, compared to embryonic stem cells, of being able to be extracted and subsequently administered to the same individual, thus minimizing the possibility of rejection.

In a preferred embodiment of the first aspect of the invention, the pluripotent stem cells additionally express CD13, c-Myc and CD90, and do not express the markers CD34, CD45, CD73 and CD44.

The researchers deposited the cells of the invention in the institution DSMZ-Deutsche Sammlung von Mikroorganismen and Zellkulturen GmbH, with the reference identification "Human dental pulp pluripotent stem cells (hDPPSC)". Subsequently, the International Depositary Authority gave the accession number DSM ACC3002.

The possibility of extracting pluripotent stem cells from dental pulp is an alternative to the sources known until now, for obtaining cells of this type with the following advantages: ease of extraction, it does not involve high risks compared to the bone marrow intervention and does not involve high costs.

Teeth are formed by two basic components: the crown and the root. A mature tooth is made up of hard tissues: enamel, dentin and cementum, as well as of a core of soft tissue known as dental pulp.

The researchers have preferably used third molars, from which the cells forming part of the invention have been isolated. Given that the third molar is the last tooth which is developed in humans, it is normally in an earlier phase of development and is capable of providing an optimal amount of dental pulp tissue for the isolation of pluripotent stem cells.

As has been mentioned, in the publication "Pluripotency of mesenchymal stem cells derived from adult marrow", Nature, 2002, vol. 418, pp. 41-47, Jiang et al. describe the isolation and the characterization of pluripotent stem cells in a cell population of the bone marrow. Unlike the cells of the invention, these cells do not express the gene CD105 and they do express the genes CD44 and CD73.

Noriaki et al., "Evaluation of Pluripotency in Human Dental Pulp Cells", J. Oral Maxillofac Surg, 2009, vol. 67, pp. 501-506, indicate in this article that they isolate pluripotent cells from dental pulp. However, in said publication the data included are not sufficient for the person skilled in the art to be able to conclude that they are pluripotent. On the contrary, the data and assays included only allow concluding that they are multipotent cells. In particular, the only assays included demonstrate the capacity to differentiate into tissues the origin of which is, for all of them, the same germ layer, the mesoderm. As has already been indicated above, there are well-established criteria which allow classifying a cell as pluripotent or multipotent. Based on the differentiations assays conducted by Noriaki et al., the person skilled in the art could only conclude that they are multipotent cells, since the differentiation into adipocyte, chondrocyte and osteocyte (tissues which are from the same germ layer) is proved and no data indicating that the isolated cells have the capacity to differentiate into tissues from the other two germ layers (endoderm and ectoderm) are provided.

In addition, the article of Noriaki et al. does not include any analysis of markers which allows determining the pluripotency of the cell. Nor does it show other characteristics typical of pluripotent cells such as their morphology, small size, high proliferative potential and high clonogenicity.

The inventors of the present invention have had to optimize a suitable growth medium in order to achieve culturing the pluripotent stem cells present in the dental pulp sample. Said medium is characterized by including the following factors: LIF, EGF and PDGF. In the Noriaki document, a culture medium specific for the growth of multipotent cells is used, which is described in the publication by Gronthos et al., "Postnatal human dental pulp stem cells in vitro and in vivo" PNAS, 2000, vol. 97, pp. 13625-13630. Example 8 of the present invention shows that it is impossible to grow pluripotent cells in an unsuitable medium, such as the medium used by Noriaki.

Due to the foregoing, the Noriaki document describes the isolation of multipotent stem cells.

The publication of Kerkis et al., "Isolation and characterization of a population of immature dental pulp stem cells expressing OCT-4 and other embryonic stem cell markers", Cell Tissues Organs, 2006, vol. 184, 105-116, states that pluripotent cells are extracted from dental pulp. However, the origin of the cells cannot be dental pulp, because the patients aged between 5 and 7 years do not have dental pulp, but rather what is referred to as dental germ, which is an aggregation of undifferentiated cells which will form the future tooth with its different parts: enamel, pulp, gum, cementum, bone, blood vessel and nerve. The origin of the cells of the invention is dental pulp, and they can be obtained from adults of any age. In addition, the medium they use to culture the cells is typical of mesenchymal cells, and the seeding technique is not suitable for culturing pluripotent cells.

With a seeding of 10,000 cells per $cm^2$, it is impossible to culture pluripotent cells due to the differentiation into fibroblasts. FIG. 1a of the Kerkis document shows cultured cells and their morphology is not typical of pluripotent cells, but rather it is a morphology typical of multipotent cells (Todorov et al. "Multipotent progenitor cells isolated from adult human pancreatic tissue" Transplant Proc., 2005 37(8), pp. 3420-1)). It is observed that the karyotype which is shown in FIG. 1e of the Kerkis document is altered, despite the fact that it is stated that it is normal. On one hand, chromosomes 1, 3 and 4 do not have the correct size. This means that the application to humans could generate tumors, which makes the use thereof in human therapy unadvisable. On the other hand, fragmented chromosomes, a common morphology in tumor cells, are observed, therefore the use thereof in human therapy seems to be unadvisable.

In a second aspect, the present invention relates to a culture comprising stem cells as they are defined in the first aspect of the invention, in a medium capable of supporting the proliferation of said cells, said culture medium including at least one transcription factor.

Media supporting the proliferation of pluripotent stem cells, such as the one described in Smith et al. (cf. Smith et al. "Inhibition of pluripotential embryonic stem cell differentiation by purified polypeptides", Nature 1988, vol. 336, pp. 688-690), are well known in the state of the art.

In a preferred embodiment of the second aspect of the invention, the growth medium comprises at least the growth factors EGF and PDGF, and the transcription factor LIF.

In a third aspect, the present invention relates to a process for obtaining the cells as they are defined in the first aspect of the invention, comprising the steps of: (a) disaggregating the tissue of the dental pulp isolated from a mammal; (b) separating the stem cells from the disaggregated tissue resulting from step (a); and (c) culturing the cells in a medium having at least one transcription factor at a seeding concentration between 40-60 cells/cm$^2$.

One of the advantages of carrying out the extraction of the cells of the invention from dental pulp, if it is compared with the extraction of stem cells from bone marrow, is that it is easier, without causing the extraction problems presented by the latter.

An advantage of the medium, which is rich in growth factors and which includes at least one transcription factor, used in the culture and process of the invention, is that genetic alterations in the cells do not occur, which allows using these cells in cell therapy for tissue regeneration.

The tissue disaggregation of step (a) of the process according to the third aspect of the invention consists of breaking the lattice of proteins which form the extracellular matrix which maintains the cells forming part of the tissue bound together. Thus, as a consequence of tissue disaggregation, a suspension of cells is eventually obtained. In order to carry out the disaggregation, processes are used which separate the proteins from the extracellular matrix (for example, sequestering the calcium ions which allow the binding), or by proteolytically breaking said proteins (by means of the action of proteases), thus achieving a suspension of the cells present in the tissue. The methods used can generally be classified in three categories:

a) mechanical methods (for example cutting, grinding, sieving, scraping, etc.). In cell cultures, methods of scraping the plate are frequently used to pull off the adhered cells.

b) chemical methods. They generally involve the addition of solutions in which there are no divalent ions or of chelating agents for these ions. In any case, the concentrations of the ions stabilizing the binding of the proteins of the extracellular matrix and of the latter with the cell receptors is reduced.

c) enzymatic methods. Treatment of the tissue or of the cell culture with solutions of active proteases (collagenase, dispase, trypsin, elastase, papain, pronase, hyaluronidase, etc.)

In a preferred embodiment of the third aspect of the invention, the tissue disaggregation takes place by means of enzymatic digestion. More preferably, the tissue disaggregation takes place by means of digestion with collagenase type I.

In order to separate the cells from the disaggregated tissue (step (b) of the process according to the third aspect of the invention), any of the standard techniques well known to the person skilled in the art can be used, such as flocculation, flotation, filtration and centrifugation, among others. In a preferred embodiment of the second aspect of the invention, the separation takes place by means of centrifuging the disaggregated tissue resulting from step (a).

The choice of one method or another for carrying out both the tissue disaggregation and the separation of the cells forms part of the routine work of the person skilled in the art.

In order to obtain DPPSC cells of the first aspect of the invention in the culture medium of the invention, the seeding must be performed at a low concentration, between 40-60 cells/cm$^2$. The inventors of the present invention have proved that at higher seeding concentrations the cells differentiate into fibroblasts, which are characterized by having a fusiform morphology and a large cytoplasm.

As has been indicated above, the fact that the cells isolated from dental pulp are pluripotent makes them interesting in tissue regeneration and/or transplantation.

Thus, in a fourth aspect of the present invention relates to a pharmaceutical composition comprising an effective amount of the stem cell according to the first aspect of the invention and a pharmaceutically acceptable carrier.

The expression "effective amount" relates to the amount of stem cell which, when administered, is sufficient to regenerate, or repair a tissue. The particular amount of cell administered according to the invention will be determined by the particular circumstances surrounding the case.

In a fifth aspect the present invention relates to a pluripotent stem cell defined in the first aspect of the invention for use in tissue regeneration or repair tissue in mammals.

In a preferred embodiment of the fifth aspect of the invention, the tissue regeneration is neuronal, liver or bone tissue regeneration.

This aspect of the invention can also be formulated as the use of a pluripotent cell as defined in the first aspect of the invention for the manufacture of a medicinal product intended for tissue regeneration or repair in mammals. The invention also relates to a method for tissue regeneration or repair in mammals, which comprises administering an effective amount of the stem cell as defined in the present invention to said mammal needing it.

The cells of the invention can also be used for the in vitro manufacture of tissue and or organs which ultimately can be transplanted to a subject.

A sixth aspect of the present invention relates to a pluripotent stem cell obtainable by means of the culture defined in the second aspect of the invention or the process defined in the third aspect of the invention.

There are a number of protocols existing in the state of the art for regenerating tissue in general, and bone, liver and neuronal tissue in particular, from pluripotent stem cells of the invention.

Techniques well known to the person skilled in the art can be used to produce bone, liver and neuronal tissue cells. For example, if differentiation into bone tissue is desired, any of the cell growth media described in Haynesworth et al. (cf. Haynesworth et al. "Characterization of cells with osteogenic potential from human marrow", Bone, 1992, vol. 13, pp. 81-88) could be used. To produce liver tissue cells, the cell growth medium described in Jiang et al. (cf. Jiang et al. "Multipotent adult progenitor cells from human bone marrow differentiate into hepatocyte-like cells induced by co-culture with human hepatocyte line", Zhonghua Yi Xue Za Zhi, 2007, vol. 87, pp. 414-418) could be used. To produce neuronal tissue cells, the cell growth medium described in Jiang et al. (cf. Jiang et al. "Multipotent progenitor cells can be isolated from postnatal murine bone marrow, muscle and brain", Exp. Hematol., 2002, vol. 30, 896-904) could be used.

The expression "use of a pluripotent cell" includes the use of a population of stem cells, which is obtained by means of the culture in a medium including at least one transcription factor. The number of cells applied will depend on the size of the tissue lesion. The application can usually be carried out by means of surgery, such that the cells of the invention can be applied directly.

Throughout the description and the claims, the word "comprises" and its variants do not intend to exclude other technical features, additives, components or steps. For the persons skilled in the art, other objects, advantages and features of the invention will be inferred partly from the description and partly from practicing the invention. The following examples and drawings are provided by way of illustration and do not intend to limit the present invention.

BRIEF DESCRIPTION OF THE DRAWINGS

and 40 (FIG. 1B).

DETAILED DESCRIPTION OF THE INVENTION

Figure 1A:
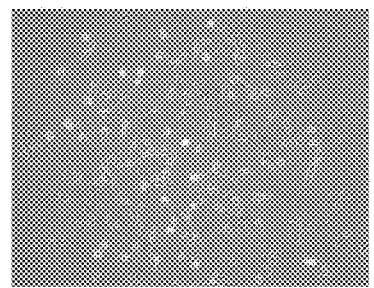
FIG. 1A and FIG. 1B show the morphology of the dental pulp pluripotent cells (DPPSCs) seen through an optical microscope with lenses of a magnification of 20 (FIG. 1A)
Figure 1B:
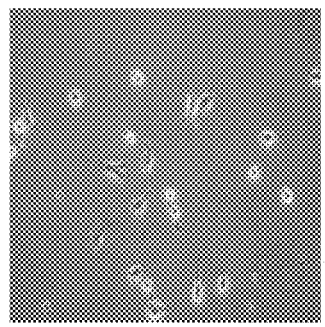
Figure 1C:
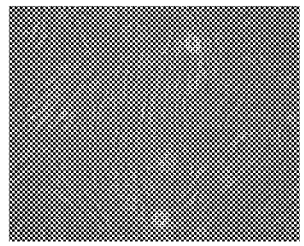
FIG. 1C and FIG. 1D show cells obtained when the culture was at a high density seen with lenses of 40 (FIG. 1C) and 100 (FIG. 1D).
Figure 1D:
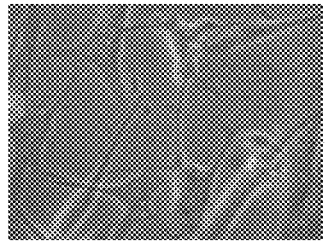

Culture Media used in the Different Examples

Medium 1. DMEM (Dulbecco's Modified Eagle Medium) used for the maintenance and transport of the samples from the operating room to the laboratory.

Medium 2. This medium is used for the culture of the DPPSC cells of the invention. The composition of the medium is 300 ml of DMEM, 200 ml of MCDB (105 Medium SIGMA), 5 ml of SITE (insulin, transferrin, sodium selenite, ethanolamine), 1 ml of LA-BSA (linoleic acid-bovine serum albumin), 5 ml of Pen/Strep (Cellgro, 30-002-CI), 5 ml of ascorbic acid, 10 ml of FBS (fetal bovine serum), 500 µl of PDGF (platelet-derived growth factor), 500 µl of EGF (epidermal growth factor), 50 µl of LIF (leukemia inhibitory factor), 0.4 g of BSA (bovine serum albumin), 5 ml of CDLC (chemically defined lipid concentrate).

Medium 3 MSC (medium for mesenchymal stem cells). Culture medium of the control cells. It is used for the culture of bone marrow MSCs and of dental pulp MSCs. The composition of the medium is DMEM (Dulbecco's Modified Eagle Minimum Essential Medium) low in glucose (DMEM-LG, Gibco Brl 11885-084), 1× Pen/Strep (Cellgro 30-002-CI), 1× (0.1 mM) L-ascorbic acid (Sigma A-8960), 2% FBS (Fetal Bovine Serum) Hyclone.

Medium 4 NTERA. It is used for the culture of the NTERA cell line. The composition of the medium is: DMEM high in glucose (DMEM-HG Gibco 41966), 2% horse serum (Gibco 26050-070), 10% FBS (Biochrom S 0115), 10% Pen/Strep (Cellgro 30-002-CI).

Medium 5 SAOS. It is used for the culture of the SAOS cells. The composition of the medium is: DMEM-HG, (Gibco 41966), 2% horse serum (Gibco 26050-070), 10% FBS (Biochrom S 0115), 10% Pen/Strep (Cellgro 30-002-CI).

Medium 6 Schwann. It is used for the culture of Schwann cells. The composition of the medium is: DMEM-LG, (Gibco 41966), 2% horse serum (Gibco 26050-070), 10% FCS (Biochrom S 0115), 10% Pen/Strep (Cellgro 30-002-CI).

Medium 7. Basal differentiation medium. The composition of the medium is: 60% DMEM-LG (GIBCO/BRL), 40% MCDB-201 (Sigma) with 1× insulin-transferrin-selenium, 1× linoleic acid BSA (albumin modified with linoleic acid), $10^{-9}$ M dexamethasone (Sigma), and $10^{-4}$ M ascorbic acid 2-phosphate (Sigma), 100 units of penicillin and 1,000 units of streptomycin (GIBCO). Differentiation media 8.

A: Hepatocyte medium: Basal differentiation medium (medium 7) with 10 ng/ml FGF-4 (R&D Systems), 100 ng/ml HGF (hepatocyte growth factor) (R&D Systems).

B: Neuron medium: Basal medium (medium 7), 100 ng/ml, basic fibroblast growth factor (bFGF) was used the first 4 days. On day 5, the medium was changed for the basal medium, FGF8 (10 ng/ml), SHH (100 ng/ml). On the eighth day: basal media, BDNF (brain-derived neurotrophic factor) (10 ng/ml), GDNF (glial cell-derived neurotrophic factor) (10 ng/ml)+N2 (R & D Systems).

C: Osteogenic medium: DMEM-LG (GIBCO/BRL), glutamine (100×), Pen/Strep (Cellgro 30-002-CI) (100×), 10% FBS, 0.01 μM 1,25-dihydroxyvitamin $D_3$ (1000×), 50 μM ascorbate-2-phosphate (1000×), 10 μM B-glycerophosphate (32.67×).

Preparation of the Sample for the Different Assays

Eight healthy human third molars from two different patients, which were extracted for orthodontic, prophylactic or periodontal reasons, were selected (Example 1-8).

Healthy human molars ($3^{rd}$ molars) were selected from 20 different patients of different ages (14-38 years), were extracted (Example 9-10).

Immediately after the extraction of the third molars, they were washed using gauze moistened with 70% ethanol and subsequently with sterile distilled water.

A cut was made between the enamel and the cementum using a cylindrical turbine burr drill, holding the tooth with forceps for upper incisors.

A fracture was performed in the same line of the cut by means of two forceps for upper incisors and the two fragments of the tooth were placed in a Falcon flask with Medium 1.

The samples were transferred to the laboratory. Once in the flow hood, the content was poured into a Petri dish.

The tissues were isolated from the dental pulp by means of a sterile size 15 broach file and sterile tweezers.

Subsequently, using an insulin syringe, the canals were washed with DMEM and the tooth fragments were discarded.

The following step was to perform the cell disaggregation by means of the digestion with collagenase type I (3 mg/ml) of the pulp tissue for 40 minutes at 37° C. and the sample was subsequently centrifuged for ten minutes at 1,800 rpm to separate the cells from the disaggregated tissue.

The cells were washed with sterile PBS (phosphate buffered saline), centrifuged again for 15 minutes at 1,800 rpm, and the cell viability was determined by means of trypan blue staining. The percentage of cell viability was about 95%.

The cells were resuspended in Medium 2. The cells obtained were incubated at 37° C. for 2-3 days in flasks previously treated with fibronectin and the occurrence of clones or cells adhered to the culture flask was evaluated. When sufficient adhered cells were observed, they were trypsinized and spread, always maintaining a low density.

Maintenance of the Cell Culture

The cells were cultured in six-well plates and treated with 10% human fibronectin in PBS (BD Bioscience) one hour before seeding the cells in the $CO_2$ incubator. In the second step, 2 ml of culture medium, referred to above as Medium 2, were added and on the fourth day 2 ml were aspirated and 2 ml of fresh medium were added. After one week, Medium 2 was changed every three days.

Isolation and Culture of Human Dental Pulp Mesenchymal Stem Cells (DPMSC)

Human adult DPMSC were isolated from dental pulp of the third molar suspended in Medium 3. Cells were plated at a density of 300.000 cells/$cm^2$, the medium was changed after 72 h and every 2 days thereafter. For propagation of MSC, cells were detached at 90% confluence by the addition of phosphate buffered saline (PBS, Biochrom) containing 0.05% trypsin-ethylenediaminetetraacetic acid (EDTA; Biocchrom) and replated at a density of 4,000 cell/$cm^2$.

Flow Cytometry (Fluorescence-Activated Cell Sorting—FACS) Analysis.

Antibodies used for the Different Assays

For the different analyses by means of flow cytometry (FACS), it was necessary to add fluorochrome-carrying antibodies to the cells (see Table 1).

TABLE 1

Monoclonal antibodies used in the FACS analysis.

| Antibody | Species | Company | Concentration |
| --- | --- | --- | --- |
| CD13 FITC | MS:MS, HUM | eBioscience | 1:50 |
| SSEA4 PE | MS:MS, HUM | eBioscience | 1:50 |
| OCT3/4 FITC | MS:MS, HUM | RD SYSTEMS | 1:50 |
| CD45 PE-Cy5 | MS:MS, HUM | BDPharmingen | 1:50 |
| CD14 PE | MS:MS, HUM | BDPharmingen | 1:50 |
| CD73 PE | MS:MS, HUM | BDPharmingen | 1:50 |
| CD29 PE-Cy5 | MS:MS, HUM | BDPharmingen | 1:50 |
| NANOG FITC | MS:MS, HUM | BDPharmingen | 1:50 |
| CD90 FITC | MS:MS, HUM | BDPharmingen | 1:50 |
| CD34 PE-Cy5 | MS:MS, HUM | BDPharmingen | 1:50 |
| CD44 | MS:MS, HUM | BDPharmingen | 1:50 |
| CD105 FITC | MS:MS, HUM | BDPharmingen | 1:50 |
| 595 rabbit IgGI | Rabbit | BDPharmingen | 1:50/1:100 |
| FITC mouse IgGI | Mouse | RD SYSTEMS | 1:50/1:100 |
| PE-Cy5 mouse IgG1 | Mouse | RD SYSTEMS | 1:50/1:100 |

MS:MS, HUM (produced in mouse, recognizes mouse and human)

IgGI antibodies bound to fluorescein isothiocyanate (FITC), phycoerythrin (PE), PE-Cy5 (BD Pharmingen) were used as a fluorescence control. The cell suspension (cells resuspended in PBS and 2% FBS) was divided into fractions of 1.5 million cells and they were incubated with the respective antibodies for 45 minutes at 4° C. and in the dark. The cells were subsequently washed twice with PBS and 2% FBS and centrifuged for 6 minutes at 1,800 rpm. This prevented the presence of fluorochrome residues, since they would give a false percentage of fluorescence.

Depending on the number of cells, the latter were resuspended in 300-600 μl of PBS and 2% FBS.

All the flow cytometry measurements were taken in the FACScan cytometer and they were analyzed by means of the winMDI 2.8 program.

Immunophenotypic Analysis

Cells were fixed with 4% paraformaldehyde (Sigma) for 4 minutes at room temperature followed by methanol (Sigma) for 2 minutes at −20° C. For nuclear ligands, cells were permeabilized with 0.1 M Triton X-100 (Sigma) for 10 minutes. Slides were incubated sequentially for 30 minutes each with primary antibody and fluorescein, PE or Cy5-coupled anti-mouse IgG antibodies. Between each step, the slides were washed with PBS plus 1% BSA (Sigma). Cells were examined by confocal fluorescence microscopy (Confocal 1024 microscope, Olympus AX70, Olympus Optical, Tokyo).

Statistical Analysis

Statistic test applied were unpaired t-test. Data were analysed with the software SPSS Version 12.0. All values were expressed as mean+/−standard deviation. Statistical significance was set at $p<0.05$

EXAMPLE 1

Characterization of the Dental Pulp Cell Cultures. Cell Morphology

Throughout the culture processes, the cells were controlled and observed under the microscope to rule out the possible contamination by yeasts, fungi or bacteria. An attempt was made to maintain a low density, taking into account the proportion of small cells (5-8 microns) with respect to the large cells (10-25 microns), for the purpose of trying to increase the number of small cells. These small cells are the cells of the invention. In the analysis of the morphology of the dental pulp stem cells, the cultures were thoroughly monitored so that they had adherent capacity, until reaching 70% confluence. FIGS. 1 (A and B) shows the appearance of the morphology of the dental pump pluripotent cells (DPPSC) seen through an optical microscope with lenses with a magnification of 20 and 40, respectively. It is important for the seeding density to be low, preferably between 40-60 cells per $cm^2$, since obtaining pluripotent cells is thus assured. FIG. 1 (B, C) shows the appearance of the morphology of the cells when the seeding density is high (80-100 cells per $cm^2$). At these seeding densities, pluripotent cells differentiate into multipotent cells, a different type of cell, of a larger size than the cells of the invention and with a fusiform morphology, being observed.

EXAMPLE 2

Phenotype Analysis of Cultured Cells in Different Passages from Dental Pulp. Flow Cytometry (FACS) Analysis This analysis was performed after one, two and three weeks of culture, for the purpose of verifying that the pluripotency nature is maintained over time. This study analyzed the phenotype of cells of different clones obtained from dental pulp samples of donors of 14, 17, 18, 28, 38 years of age cultured at a low density, 40 to 60 cells per $cm^2$, and after spreading them when the culture reaches 70% culture confluence.

The FACS analysis was performed every week for each of the cultures of cells from the clones (14, 17, 18, 28, 38 years) during the three weeks of culture to see the change of percentage of markers specific for pluripotency. The antibodies CD13 FITC, SSEA4 PE, OCT3/4 FITC were used. More than 200,000 cells per sample were analyzed to detect non-specific binding or autofluorescence. Non-specific binding was not detected. A decrease in the presence of markers specific for DPPSCs with the increase of age was also observed, although they increased during the culture (see Table 2).

TABLE 2

FACS analysis for determining the phenotype of the cultured cells in different passages from dental pulp.

| | | PAT Y | PAT 14 | PAT 17 | PAT 18 | PAT 28 | PAT 38 | MEAN |
|---|---|---|---|---|---|---|---|---|
| CD13 | First | 16.9 | 15.2 | 20 | 22.1 | 21.7 | 19.18 |
| SSEA-4 | Week | 15.7 | 6.3 | 5.7 | 2.8 | 2.1 | 6.52 |
| OCT3/4 | | 0.9 | 0.7 | 0.2 | 0.08 | 0.08 | 0.392 |
| CD13 | Second | 18.4 | 30 | 27 | 52.2 | 48.75 | 35.27 |
| SSEA-4 | week | 15.9 | 7.1 | 6.3 | 5.4 | 5.15 | 7.97 |
| OCT3/4 | | 1.1 | 0.9 | 0.5 | 0.8 | 0.6 | 0.78 |
| CD13 | Third | 98 | 30.9 | 38.7 | 54.2 | 51.2 | 54.6 |
| SSEA-4 | week | 51.7 | 55.6 | 25. | 8 | 10.6 | 30.22 |
| OCT3/4 | | 16.3 | 8.2 | 2.3 | 1.2 | 0.9 | 5.78 |

PAT Y: patient of age Y.

An increase is observed in the percentage of markers specific for pluripotent cells, DPPSCs, cultured at a low cell density as the culture time increases. It can be concluded that over time the cells maintain the pluripotent nature, therefore they may be interesting in tissue regeneration, repair or transplantation therapies.

An additional FACS analysis using the sample from the donor of 14 years of age in the third week of culture was also performed. In addition to the markers CD13, SSEA4, OCT3/4, the markers CD45, CD73, CD105, CD34 were analyzed. Table 3 shows the results.

TABLE 3

Phenotype of the DPPSCs of a sample from the patient of 14 years of age. Sample 14 years

| | |
|---|---|
| CD105 | 93.3% |
| CD45 | 0% |
| CD73 | 0% |
| CD14 | 8% |
| CD44 | 0% |
| CD90 | 42% |
| CD13 | 98% |
| SSEA4 | 51% |
| OCT3/4 | 16% |
| CD34 | 0% |

As is inferred from Table 3, the DPPSC cells of the invention express the markers specific for pluripotent cells CD105, CD14, CD90, CD13, SSEA4, OCT3/4 and do not express the markers CD45, CD73, CD44 and CD34 which are specific for multipotent cells. Therefore, it is demonstrated that the cells of the invention are of the pluripotent type.

EXAMPLE 3

Phenotype Analysis of SSEA4-Positive Cells Separated by a Flow Cytometer (Cell Sorter)

A dental pulp sample was extracted from a patient of 18 years of age. Then, the populations positive for CD13 FITC (eBioscience) and SSEA4 PE (eBioscience) were isolated by FACS, and the population doubly positive for CD13 and SSEA4 was also isolated. The cells were collected in 24-well culture plates. The separation by FACS was performed in a Coulter, EPICS ELITE-ESP®.

The separation, by means of flow cytometry, of the population of SSEA4-positive (SSEA4+) cells contained in the original dental pulp sample obtained on the same day of the extraction was performed. The phenotype of these cells was studied and compared with that of the DPPSC cells cultured but not selected by flow cytometry.

The separation or the isolation was performed in a flow cytometer with a cell separating device, EPICS ELITE-ESP®.

250 SSEA4-positive (SSEA4+) cells were separated. These cells were cultured in a 90-well plate and treated with human fibronectin (BD Bioscience) one hour before seeding the cells in the incubator at 37° C. and 5% $CO_2$. In each well, 10 cells were seeded with 150 ml of Medium 2.

Figure 2:
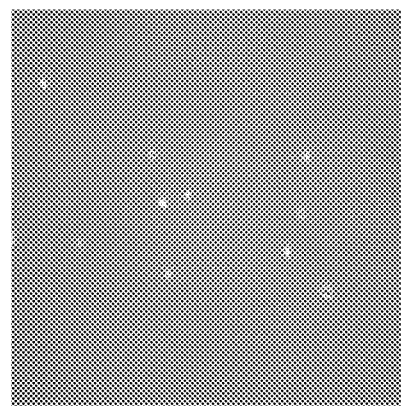
FIG. 2 shows a conventional microscope image (20×) showing the morphology of cells selected or separate in Example 3 of the invention after four days of culture.

The cells thus separated survived the process and proliferated until obtaining subconfluent wells. They also had a morphology very similar to the dental pulp DPPSCs not separated by cytometry (see FIG. 2).

The phenotype of these cells was also determined by means of markers, being similar to the dental pulp cells not separated by cytometry (Example 2). See Table 4.

TABLE 4

FACS phenotype analysis of the SSEA4-positive cells isolated by a cytometer (cell sorter)

| CD105 | CD45 | CD13 | SSEA4 | OCT3/4 | CD34 |
|---|---|---|---|---|---|
| 95% | 0% | 95% | 51% | 12% | 0% |

It is inferred from this table that the cell isolation process by means of a cytometer (cell sorter) does not improve the purity or homogeneity of the DPPSCs obtained by means of the in vitro culture during different passages.

EXAMPLE 4

Analysis of the Expression of the Genes NANOG and SOX2, Specific for Pluripotency in DPPSC Cells by Means of Q-RT-PCR (Quantitative Reverse Transcription Polymerase Chain Reaction)

The SYBR Green system was used to determine the expression of genes by means of Q-RT-PCR.

In this system, the reaction was carried out in a total volume of 22 µl, 20 µl of mix (SYBR Green supermix) and 2 µl of complementary DNA (cDNA) sample. The samples were subjected to 40 cycles after a denaturing cycle of 2 minutes at 50° C. A positive control (NTERA cells, donated by Dr. Miguel Barajas of the Universidad de Navarra) and negative control (MSC cells) for each sample, as well as a GAPDH (glyceraldehyde-phosphate-dehydrogenase) loading control were used in all the cases.

The expression of NANOG and SOX-2 in the DPPSC dental pulp cells of the clone of the patient of 14 years of age was demonstrated by means of Q-RT-PCR, and the expression of these genes in passage 5, 10, 15 was compared using NTERA cells as the positive control and pulp MSCs as the negative control.

Figure 3:
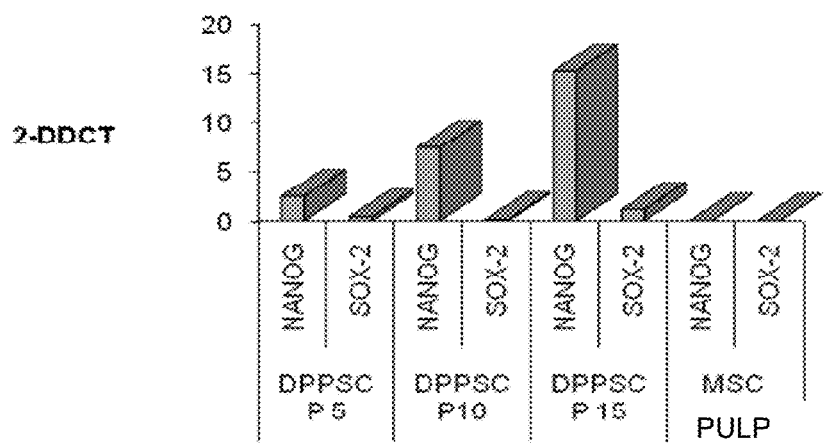
FIG. 3 shows the expression of the pluripotent markers NANOG and SOX2 in DPPSC at different passages (P5, P10 and P15) by means of Q-RT-PCR. MSC from dental pulp were used as a negative control.

It was observed that the expression of NANOG and SOX-2 increased between passages 5, 10 and 15. See FIG. 3. The expression of these genes is essential for allowing the proliferation of the cells without their differentiation, maintaining their renewal capacity, like embryonic stem cells.

The efficiency of amplification of each gene in the NTERA cells at different concentrations of cDNA (1, 0.1, 0.01, 0.001, 0.0001) was previously analyzed. It was observed that the amplification of cDNA was linear between 19.98 to 28.46 cycles for GAPDH, between 24.15 to 30.73 cycles for NANOG, and between 25.30 to 31.27 cycles for SOX-2. The amplification slopes of the genes were: GAPDH $y=3.0196x+14.412$, $R^2=0.97$. NANOG $y=3.2878x+20.841$, $R^2=0.9999$. Sox2 $y=2.9832x+22.563$, $R^2=0.9802$.

The sequences of the primers and probes used are described below:

```
Detection of GADPH by SYBR Green:
Forward primer (SEQ ID NO 1):
5'TGGTATCGTGGAAGGACTCATGAC3'

Reverse primer (SEQ ID NO 2):
5'ATGCCAGTGAGCTTCCCGTTCAGC3'

Detection of SOX-2 by the SYBR Green system:
Forward primer (SEQ ID NO 3):
5'GGGAAATGGGAGGGGTGCAAAAGAGG3'

Reverse primer (SEQ ID NO 4):
5'TTGCGTGAGTGTGGATGGGATTGGTG3'

Detection of NANOG by the SYBR Green system:
Forward primer (SEQ ID NO 5):
5'AAAGAATCTTCACCTATGCC3'

Reverse primer (SEQ ID NO 6):
5'GAAGGAAGAGGAGAGACAGT3'
```

EXAMPLE 5

Differentiation of Dental Pulp Cells

For the purpose of determining the pluripotency of the dental pulp DPPSCs, the potential for in vitro differentiation into tissues of each of the three germ layers, mesoderm, endoderm and ectoderm, was analyzed.

Mesodermal Differentiation. Differentiation into Osteoblasts.

The cells to be differentiated were seeded in 24-well plates in the culture medium at a density of $3\times10^3$ cells per cm$^2$ in basal medium. The next day the culture medium was changed for differentiation medium, referred to in this patent as C: Osteogenic medium, in the section "culture media used in the different examples". The medium was changed every 3 days for 10 days. By means of Q-RT-PCR techniques it was demonstrated that these cells had differentiated into bone tissue, expressing genes specific for this tissue, such as osteocalcin. To determine the presence of osteocalcin in the Q-RT-PCR the sequence (SEQ ID NO 7) 5'GGTGCAGAGTCCAG-CAAAGG3' was used as the forward primer and the sequence (SEQ ID NO 8) 5'AGCGCCTGGGTCTCTTCCTA3' as the reverse primer.

Figure 5:
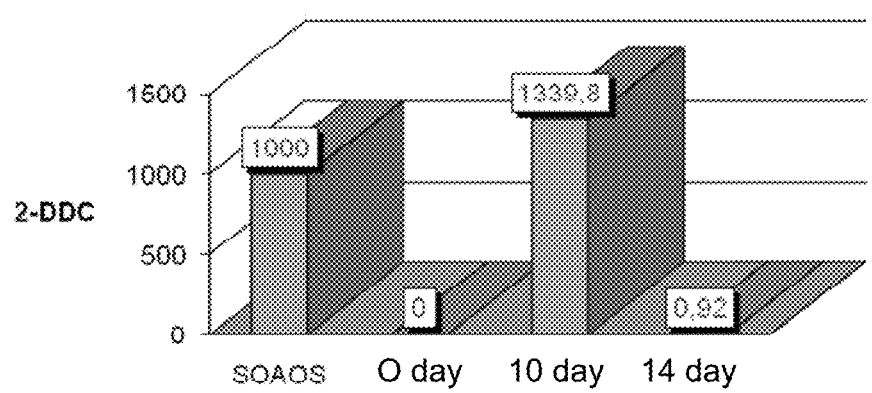
FIG. 5 shows the expression of osteocalcin by means of Q-RT-PCR on days 0, 10 and 14 with respect to the positive control (SAOS, osteoblast cells), which is given a value of 1000.

SAOS cells were used as the positive control (donated by Dr. Miguel Barajas of the Universidad de Navarra) and undifferentiated DPPSC dental pulp cells as the negative control and GAPDH as the constitutive gene (HK). As observed in FIG. 5, the concentration of osteocalcin is increased on day 10 with respect to day 0.

Figure 4:
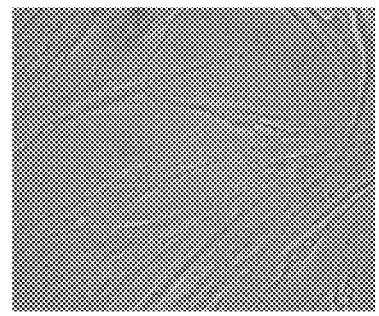
FIG. 4 shows a conventional microscope image (40×) showing the morphology of the cells of the invention differentiated into osteoblasts on day 4.

FIG. 4 also shows the differentiation into osteoblasts through a conventional microscope, the cells showing the morphology typical of said cell type.

Figure 12A:
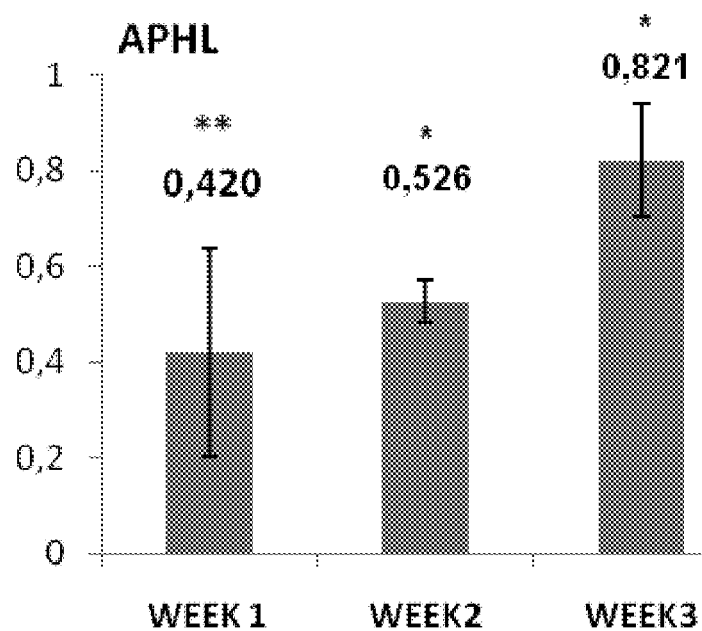
FIGS. 12A-C show the expression of APHL (FIG. 12A), osteonectin (FIG. 12B) and osteocalcin (FIG. 12C) by means of Q-RT-PCR during the three weeks of differentiation. Human bone was used as the positive control, the values are represented in relation to day 0 of differentiation, which is standardized as 1.
Figure 12B:
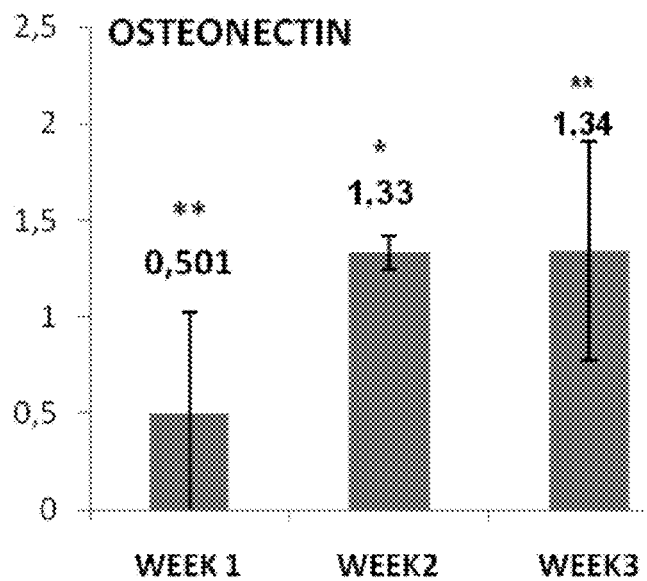
Figure 12C:
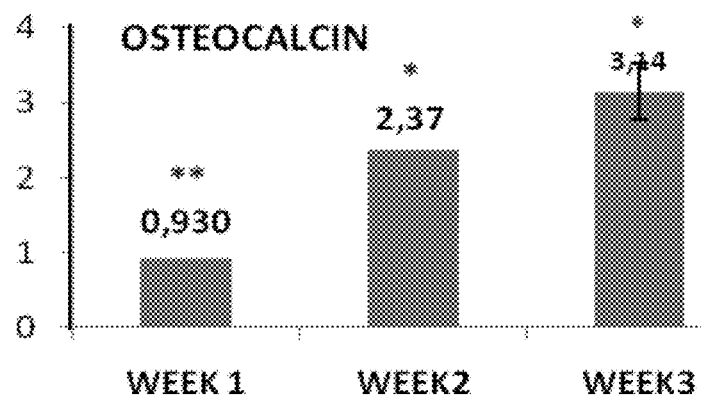

The same assay was performed, but extending its period to 21 days. The medium was changed every three days in the same way as in the previous case. Osteocalcin (FIG. 12C), osteonectin (FIG. 12B) and APHL (FIG. 12A), since they are genes specific for bone tissue, and NANOG, were determined every week. The concentration of osteocalcin, osteonectin and APHL increases over the weeks, mesodermal differentiation being demonstrated. The disappearance of the expression of the gene NANOG over three weeks of differentiation is also analyzed. Human bone cDNA (Ambion) was used as the positive control and GADPH as the loading control (HK).

The primers used in the amplification were the following: for APHL, (SEQ ID NO 13) 5'GAAGGTGAAGGTCG-GAGTCA3' as the forward primer and (SEQ ID NO 14) 5'TGGACTCCACGACGTACTCA3' as the reverse primer, for osteocalcin the same as in the previous case, (SEQ ID NO 7) and (SEQ ID NO 8), and for osteonectin (SEQ ID NO 15) 5'AGGTATCTGTGGGAGCTAATC3' as the forward primer and (SEQ ID NO 16) 5'ATTGCTGCACACCTTCTC3' as the reverse primer. For NANOG the forward primer was (SEQ ID NO 5) and the reverse primer was (SEQ ID NO 6).

The RT-PCR was performed in CFX96 (Bio-Rad), using 50 ng of cDNA and SYBR Green Supermix (Bio-Rad Laboratories). The cDNA samples were amplified using the specific primers under the following conditions, 50° C. 2 minutes, 95° C. 10 minutes, 95° C. 0.15 minutes, 60° C. 1 minute (40 cycles), 72° C. 1 minute, denaturation curve from 65° C. to 95° C.

The results indicate that the DPPSC cells can differentiate into bone tissue since they express genes specific for this tissue.

Figure 7:
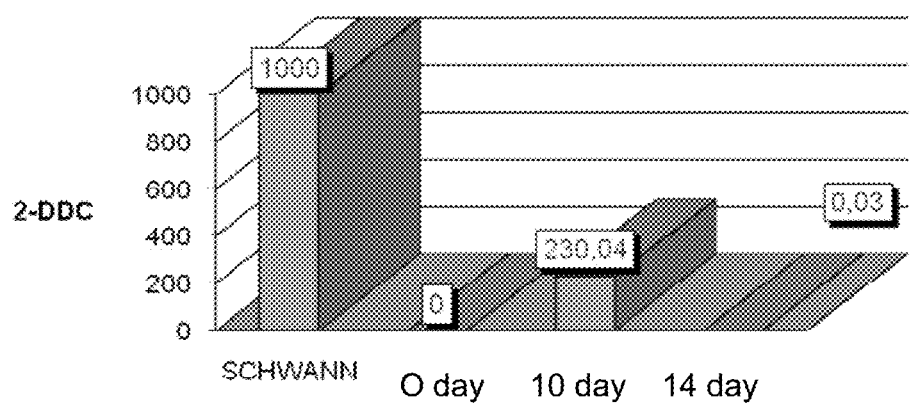
FIG. 7 shows the expression of nestin by means of Q-RT-PCR on days 0, 10 and 14 with respect to the positive control (Schwann), which is given a value of 1000.

Ectodermal Differentiation. Differentiation into Neurons:

The cells to be differentiated were seeded in 24-well plates in the culture medium at a density of 25-30 cells per cm$^2$ in basal medium. The next day the culture medium was changed for differentiation medium, referred to in the present application as B: Neuron medium, in the section "Culture media used in the different examples". In the Q-RT-PCR Schwann cells (donated by Dr. Miguel Barajas of the Universidad de Navarra) were used as the positive control and GAPDH as the loading control (HK). As observed in FIG. 7, the concentration of NESTIN, a neuronal tissue marker, increased on day 10 with respect to day 0.

To determine the NESTIN in the Q-RT-PCR the sequence (SEQ ID NO 9) CAGGAGAAACAGGGCCTACA was used as the forward primer and the sequence (SEQ ID NO 10) TGGGAGCAAAGATCCAAGAC as the reverse primer.

Figure 6:
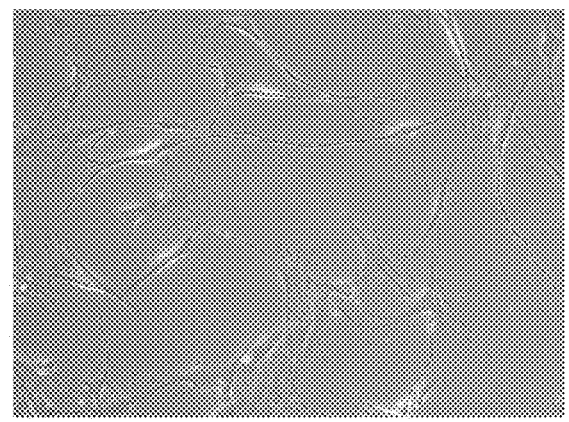
FIG. 6 shows a conventional microscope image (40×) showing the morphology of the cells of the invention differentiated into neurons on day 4.

FIG. 6 also shows the differentiation into neurons through a conventional microscope, the cells showing the morphology typical of neurons.

Figure 14A:
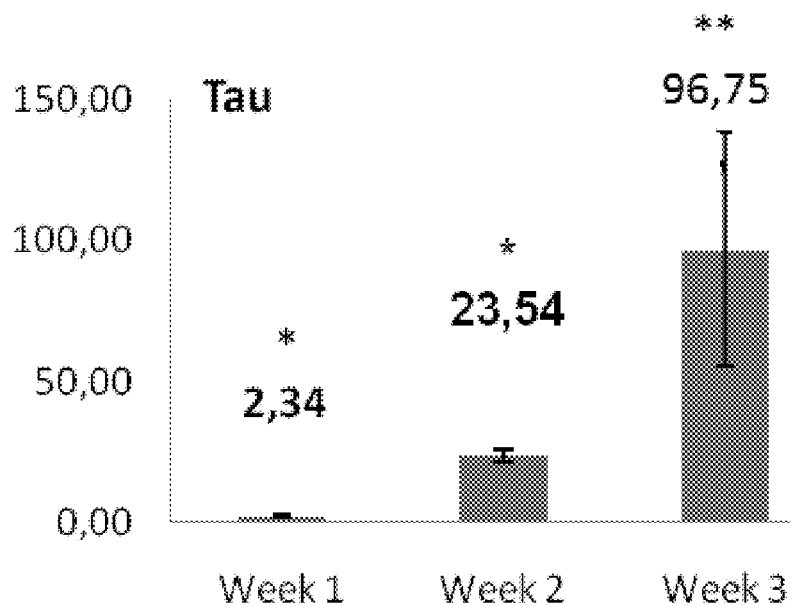
FIGS. 14A-C show the expression of Tau (FIG. 14A), Nurr-1 (FIG. 14B) and Nestin (FIG. 14C). Human brain was used as the positive control, the values are represented in relation to day 0 of differentiation, which is standardized as 1.
Figure 14B:
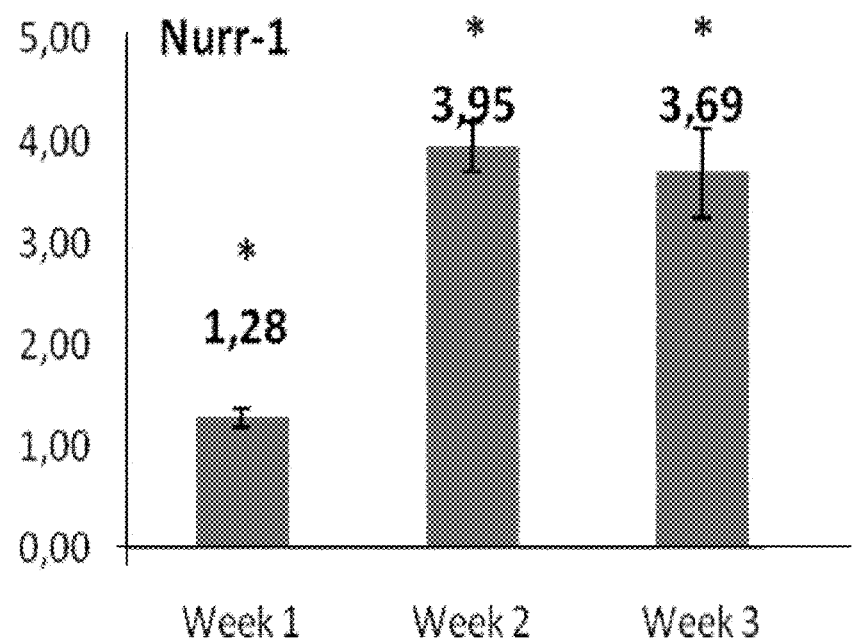
Figure 14C:
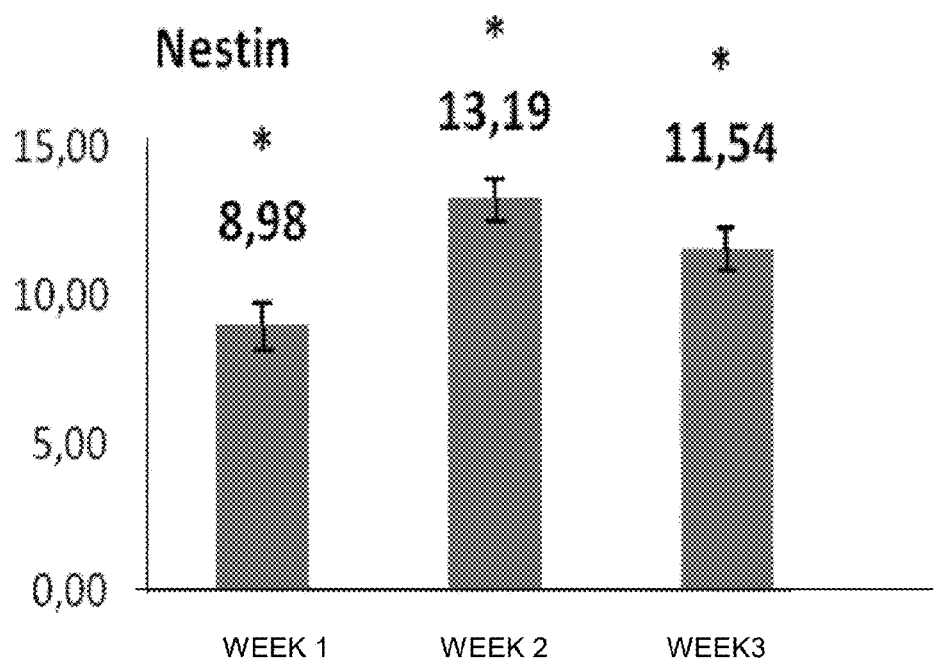

The same assay was repeated for 21 days. The expression of genes specific for neuronal tissue, such as Tau (FIG. 14A), Nestin (FIG. 14C) and Nurr1 (FIG. 14B) and NANOG, were determined every week. The concentration of the three markers increases over the three weeks. The disappearance of the expression of the gene NANOG over the three weeks of differentiation was also analyzed. Human brain cDNA (Ambion) was used as the positive control and GADPH as the loading control (HK).

The primers used in the amplification were the following: for nestin and NANOG the same as in the previous examples, for Tau, (SEQ ID NO 17) 5'TCCAGTCGAAGAT-TGGGTCC3' as the forward primer and (SEQ ID NO 18) 5'GCTTGTGGGTTTCAATCTTTTTATTT3' as the reverse primer, and for Nurr1 (SEQ ID NO 19) 5'GCTGTTGG-GATGGTCAAAGAAG3' as the forward primer and (SEQ ID NO 20) 5'GGTTTCGAGGGCAAACGA3' as the reverse primer.

The RT-PCR was performed in CFX96 (Bio-Rad), using 50 ng of cDNA and SYBR Green Supermix (Bio-Rad Laboratories). The cDNA samples were amplified using the specific primers under the following conditions, 50° C. 2 minutes, 95° C. 10 minutes, 95° C. 0.15 minutes, 60° C. 1 minute (40 cycles), 72° C. 1 minute, denaturation curve from 65° C. to 95° C.

The results indicate that the DPPSC cells can differentiate into neuronal tissue since they express genes specific for this tissue.

Endodermal Differentiation. Differentiation into Hepatocytes.

Figure 9:
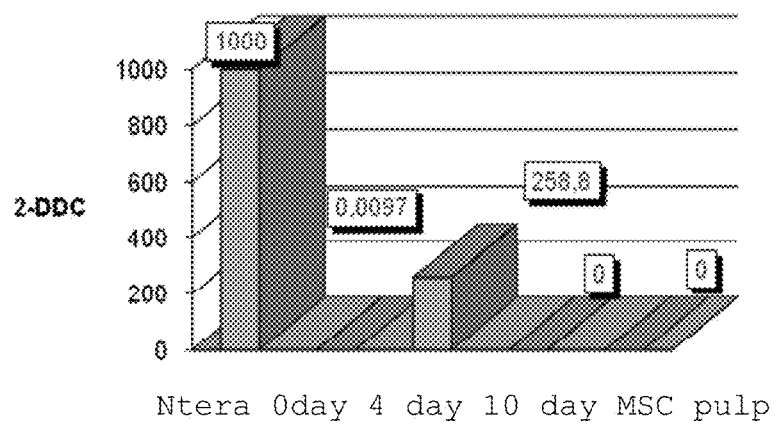
FIG. 9 shows the expression of HNF3 (Hepatocyte Nuclear Factor) by means of Q-RT-PCR on day 4 and day 10 with respect to the positive and negative controls. The results are shown in relation to the positive control (NTERA), which is given a value of 1000.

The cells to be differentiated were seeded in 24-well plates in the culture medium at a density of 25×10$^3$ cells per cm$^2$ in basal medium. The next day the culture medium was changed for differentiation medium, referred to in the present application as "A: Hepatocyte medium", in the section "Culture media used in the different examples". The medium was changed every 3 days for 10 days. By means of Q-RT-PCR techniques it was determined that these cells had differentiated into liver tissue, expressing genes specific for this tissue such as HNF3 (hepatocyte nuclear factor). NTERA cells were used as the positive control and GAPDH as the loading control (HK). As observed in FIG. 9, the concentration of HNF3 is increased on day 4 with respect to day 0.

To determine the presence of HNF3 in Q-RT-PCR the sequence (SEQ ID NO 11) 5'CAGGAGAAACAGGGC-CTACA3' was used as the forward primer and the sequence (SEQ ID NO 12) 5'TGGGAGCAAAGATCCAAGAC3' as the reverse primer.

Figure 8:
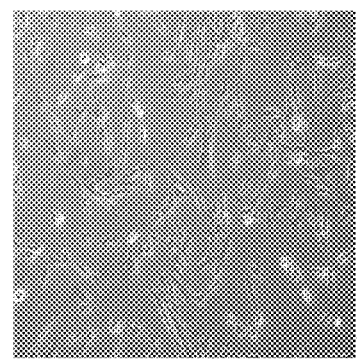
FIG. 8 shows a conventional microscope image (40×) showing the morphology of the cells of the invention differentiated into hepatocytes on day 4.

FIG. 8 also shows the differentiation into hepatocytes through a conventional microscope, the cells showing the morphology typical of this type of cell.

Figure 13A:
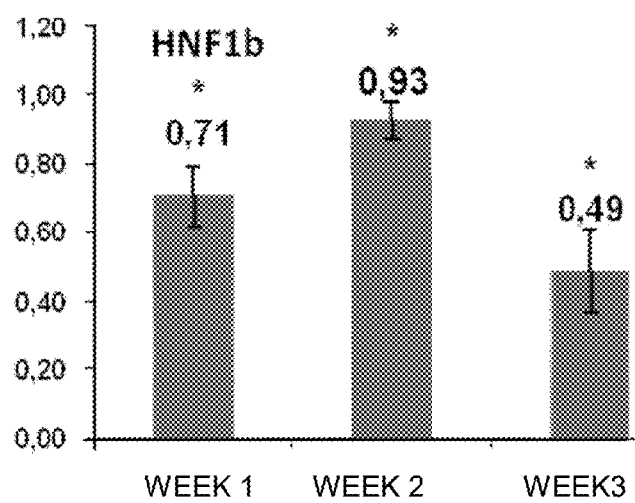
FIGS. 13A-C show the expression of HNF1b (FIG. 13A), HNF6 (FIG. 13B) and GATA (FIG. 13C). Human liver was used as the positive control, the values are represented in relation to day 0 of differentiation, which is standardized as 1.
Figure 13B:
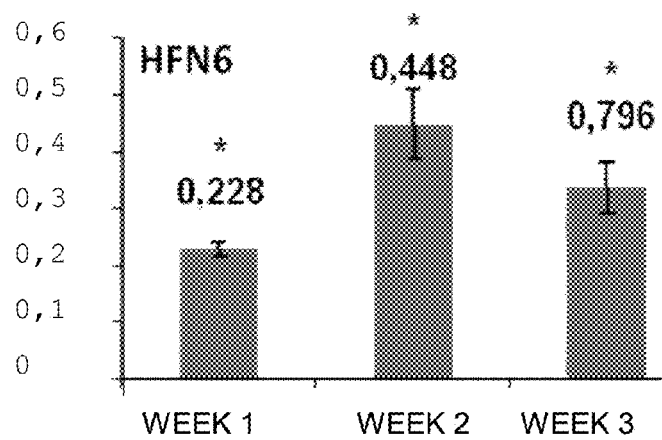
Figure 13C:
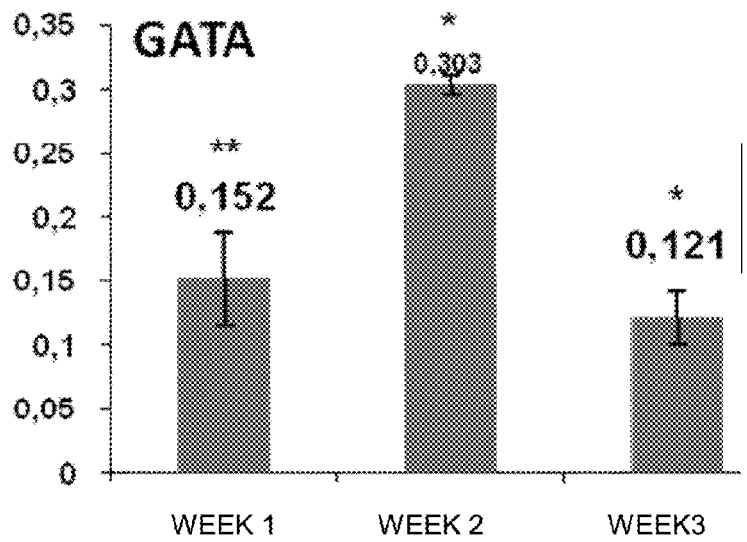

The same assay was repeated for 21 days. The levels of hepatic nuclear factors (HNF1beta, HNF6), and GATA since they are genes specific for liver tissue, were determined every week. The concentration of HNF1beta increased in the first week and the expression of this gene decreased in the second and third week, but the expression of HNF6 increased, endodermal differentiation being demonstrated. Human liver cDNA (Ambion) was used as the positive control and GADPH as the loading control (HK) (FIG. 13).

The primers used in the amplification were the following: for HNF6, (SEQ ID NO 21) 5'CTTAGCAGCATG-CAAAAGGA3' as the forward primer, and (SEQ ID NO 22) 5'TGCGTTCATGAAGAAGTTGC3' as the reverse primer, for HNF1beta (SEQ ID NO 23) 5'ATTGCTGGTCGTTTGT-TGTG3' as the forward primer and (SEQ ID NO 24) 5'TACGTGTTCATGCCGTTCAT3' as the reverse primer, for GATA, (SEQ ID NO 25) 5'TCCCTCTTCCCTCCTCAAAT3' as the forward primer, and (SEQ ID NO 26) 5'TTC-CCCTAACCAGATTGTCG3' as the reverse primer and for GAPDH (SEQ ID NO 1) as the forward primer and (SEQ ID NO 2) as the reverse primer.

The RT-PCR was performed in CFX96 (Bio-Rad), using 50 ng of cDNA and SYBR Green Supermix (Bio-Rad Laboratories). The cDNA samples were amplified using the specific primers under the following conditions, 50° C. 2 minutes, 95° C. 10 minutes, 95° C. 0.15 minutes, 60° C. 1 minute (40 cycles), 72° C. 1 minute, denaturation curve from 65° C. to 95° C.

The results indicated that the DPPSC cells can differentiate into liver tissue since they express genes specific for this tissue.

The presence of NANOG was determined in each of the mesodermal, endodermal and ectodermal differentiation assays. It was not expressed after the second week in any of the three cases. This result is remarkable because the prolonged expression over time of the gene NANOG could be related to tumorigenicity.

EXAMPLE 6

Cytogenetic and Electron Microscopy Study of the DPPSCs of the Invention

A cytogenetic and scanning electron microscopy (SEM) (Zeiss EM900) study was performed every week. To perform the electron microscopy, a 1 mm$^3$ section of cell pellet was fixed in a solution of formaldehyde (2%), glutaraldehyde (2.5%) and with Karnofsky's buffer with cacodylate (0.2 mol/L, pH 7.4). After 48 hours, the samples were embedded in araldite. The ultra-thin sections were contrasted with citrate and observed under the electron microscope (Zeiss EM900).

The study was performed to see if there were chromosome abnormalities or cell structure changes of the culture. This was performed for the purpose of clinically applying these cells in the future as cell therapy for tissue regeneration.

Figure 10:
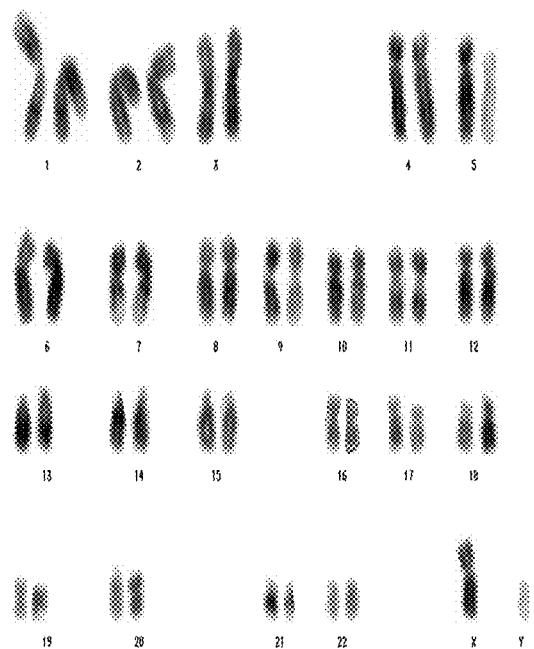
FIG. 10 shows the cytogenetic study of the DPPSC cells of the dental pulp in passage 15.

FIG. 10 shows the results of the cytogenetic and SEM study and it can be seen that neither abnormalities nor fragmentation of chromosomes or of cell structures are observed. For this study 200 metaphases were analyzed and more than 85% of the cells were observed without abnormalities or fragmentations. Chromosome breaks were observed in 15% of the remaining metaphases, which are usual as a consequence of the technique used. It is a remarkable fact that abnormalities or structural changes have not been detected in the chromosomes of the cells of the invention, this fact indicates that the cells of the invention are active, being capable of differentiating into any tissue from the three germlines.

EXAMPLE 7

Comparison of the Phenotype by the Expression of Different Markers of Different Types of Cells The expression or non-expression of the genes shown in Table 5 was compared by means of the FACS of the cells of the invention, DPPSC, MAPSC (donated by Dr. Miguel Barajas of the Universidad de Navarra), MSC (mesenchymal stem cells), IPS (induced pluripotent stem) and NTERA.

TABLE 5

The expression (+) or non-expression (−) of the different markers in the different types of cells studied. The "?" shows non-assayed markers.

|       | DPPSC | MAPSC | MSC | IPS | NTERA |
|-------|-------|-------|-----|-----|-------|
| OCT3/4 | + | + | +/− | + | + |
| SSEA4 | + | + | − | + | + |
| CD13  | + | + | + | + | + |
| SOX-2 | + | ? | − | + | + |
| NANOG | + | ? | − | + | + |
| C-Myc | + | ? | − | + | + |
| CD44  | − | + | + | ? | ? |
| CD90  | + | + | + | ? | ? |
| CD105 | + | − | − | ? | ? |
| CD73  | − | + | + | ? | ? |
| CD45  | − | − | + | ? | ? |

From the results of Table 5 it is concluded that the cells of the invention have an expression profile of specific markers and different from that obtained for the MAPSC and MSC cells.

EXAMPLE 8

Comparative Assay of Culture Media

Figure 11A:
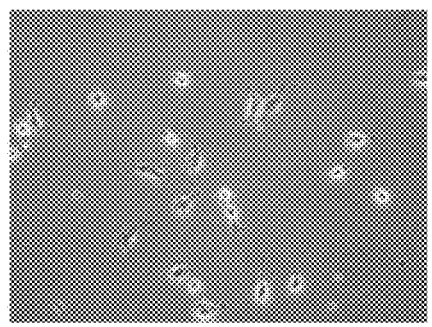
FIG. 11A (Medium 2) and FIG. 11B (Medium 3) show conventional microscope images showing the results of Example 8.
Figure 11B:
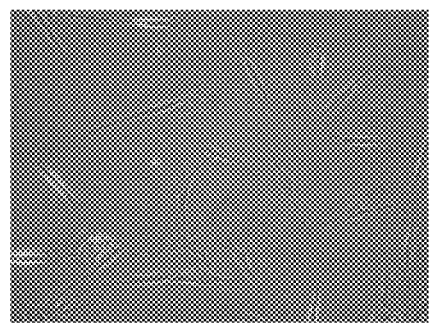

A comparison was made between Medium 2 (the medium for DPPSCs) and Medium 3 (MSC medium) for the purpose of determining which of them allowed obtaining the pluripotent stem cells of the present invention. To that end, a dental pulp sample of the same patient was used. On the same day, the sample was divided into two parts; one part was placed in the MSC medium and the other part in the DPPSC medium. It was maintained with the same seeding concentration for 3 weeks and the large difference of morphology and of phenotype was observed. In particular, it is observed that the cells which were placed in Medium 2 are small, between 5 and 8 microns, a morphology typical of the cells of the invention, whereas those which were placed in Medium 3 are larger in size and elongated. This demonstrates that the DPPSC cells can only live in their described medium. FIG. 11 shows the cells which were cultured in Medium 2 on the left (FIG. 11A) and the cells which were cultured in Medium 3 on the right (FIG. 11B).

EXAMPLE 9

Immune-Phenotype by FACS Analysis

Figure 15A:
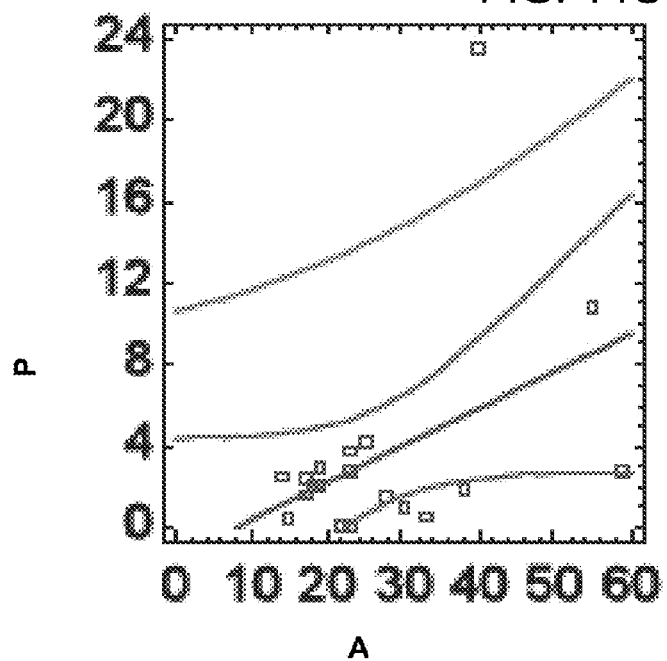
FIGS. 15A-C show the immuno-phenotype by FACS analysis of fresh dental pulp population. Expression of main surface markers SSEA4 (FIG. 15A), OCT3/4 (FIG. 15B) and NANOG (FIG. 15C) are also shown as an average of total donors analysed (n=20) in a plot age (A) versus percentage (P).
Figure 15B:
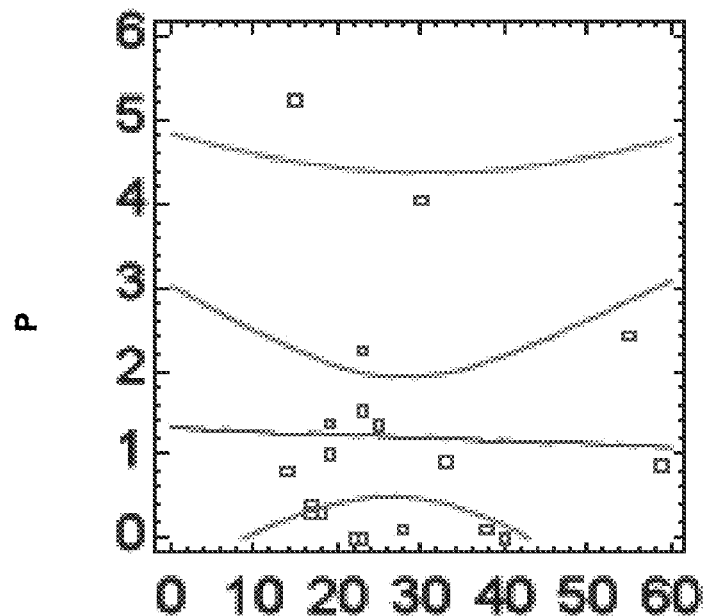
Figure 15C:
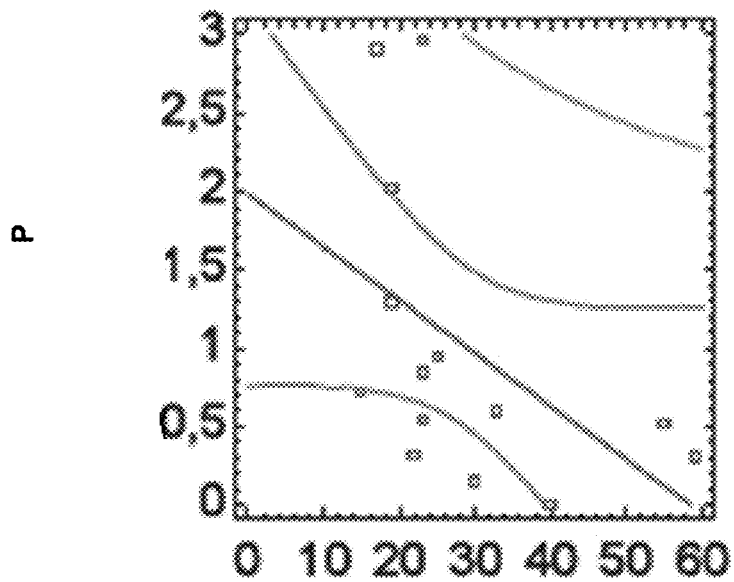

Immuno-phenotype by FACS analysis was realized, of fresh dental pulp population obtained from the third molar of representative donors at different ages directly after the dental extraction. It was examined the expression of the presence of the pluripotency markers SSEA, Oct3/4 and NANOG (FIG. 15) of the pulp tissue from donors at different ages on the same say of the extraction (n:20 samples), as representing the presence of the subpopulation DPPSC, it was observed that all the samples analyzed showed the presence of DPPSC.

The average percentage of all expression, revealed that there was expression for the markers SSEA4, Oct3/4 and Nanog. In order to relate the behavior of specific markers for DPPSC, according to the patient's age, the percentages found were subjected to regression analysis, considering the independent variable (age) and the dependent variable (different markers). The correlation analysis taking into account the variables Age-SSEA4 showed a p-value of 0.06 (significant) and a correlation coefficient of 0.43 showing an increase in the percentage of SSEA4 as age increase. Correlation Age-Oct3/4 with a p-value of 0.8 (not significant) and a correlation coefficient of −0.034 which indicated a decrease in the percentage of Oct3/4 as the age increase, but the decrease was not significant. According to our results Oct3/4 expression was maintained constantly at different ages. Finally, correlation age-nanog, with a p-value of 0.08 (significant) and a correlation coefficient of −0.48 showing a decrease in the percentage of Nanog as age increases.

EXAMPLE 10

Expression of Markers by Means of Q-RT-PCR

Total cellular RNA samples were extracted from DPPSC in passes 5, 10 and 15 (hereinafter referred as P5, P10, P15, respectively), H-Ntera, HDPMSC, and every week from differentiated cells, using Trizol (Invitrogen). 2 µg of RNA were treated with DNase I (Invitrogen) and reverse-transcribed using M-MLV Reverse transcriptase (Invitrogen). We analysed the efficacy, at different concentrations of the cDNA (1, 0.1, 0.01, 0.001, 0.0001 dilutions) for all primers of pluripotent genes, using NTERA cells as positive controls. Quantitative RT-PCR was done on CFX96 (Bio-Rad). Real-Time polymerase chain reactions were performed using 50 ng of cDNA and SYBR Green Supermix (Bio-Rad Laboratories, Inc.). cDNA samples were amplified using specific primers following the conditions: 50.0° C. for 2:00/95.0° C. for 10:00/95.0° C. for 0:15/60.0° C. for 1:00/(40 cycles) 72.0° C. for 1:00/Melt Curve 65° C. to 95° C.: Increment 0.5° C. for 0:05. The expression of genes of interest (SEQ. ID. NO 1, SEQ. ID. NO 2, SEQ. ID. NO 3, SEQ. ID. NO 4, SEQ. ID. NO 5, SEQ. ID. NO 6 and the primers used in the amplification for Oct3/4, (SEQ ID NO 27) 5'GACAGGGGGAGGGGAG-GAGCTAGG3' as the forward primer, and (SEQ ID NO 28) 5'CTTCCCTCCAACCAGTTGCCCAAAC3' as the reverse primer) was normalised against the housekeeping gene GAPDH in all samples, and relative gene expression was analyzed with the 2_ΔΔCt method.

Figure 16A:
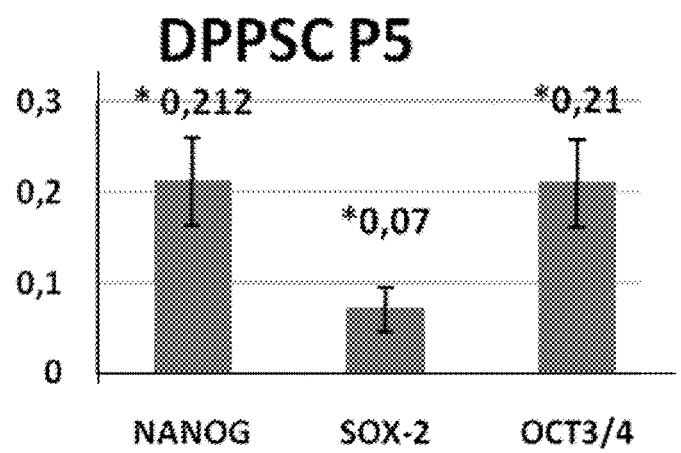
FIGS. 16A-C show the expression of pluripotent markers NANOG, SOX2 and OCT3/4 in DPPSC at different time-points (P5 (FIG. 16A), P10 (FIG. 16B) and P15 (FIG. 16C)) by means of Q-RT-PCR (Positive control Ntera which is normalized as 100).
Figure 16B:
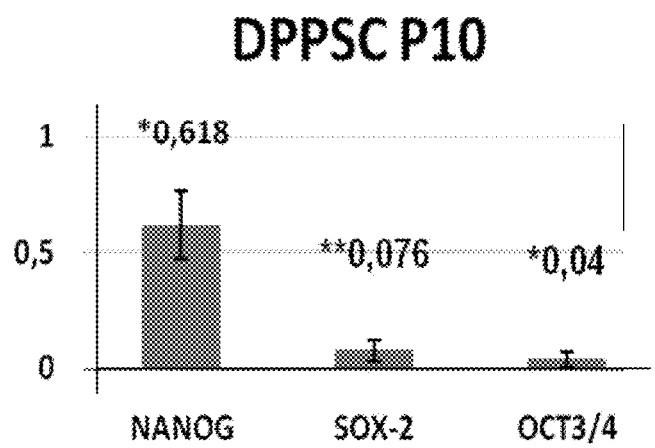
Figure 16C:
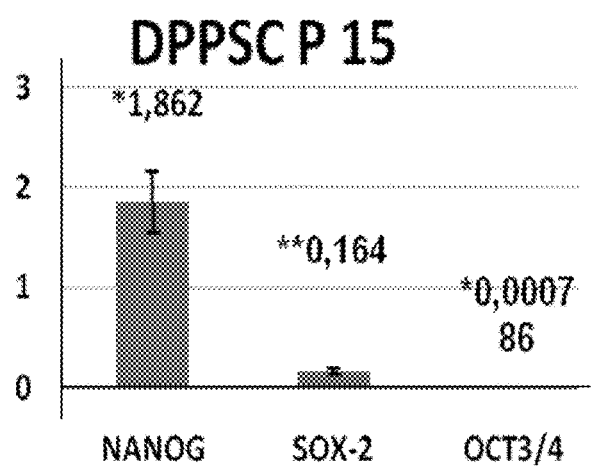

Through Q-RT-PCR was demonstrated the expression NANOG, SOX.2 and Oct3/4 in the DPPSC cells and the comparison of expression of these genes was done in passes 5, 10 and P15, using the NTERA cells as positive control and MSC-derived from dental pulp as negative control. It can be observed that the expression of the NANOG and SOX-2 increases between passes 5, 10 and 15. In contrast, it was observed that the expression of Oct3/4 was reduced in P10 and P15 (FIG. 16)

EXAMPLE 11

Characterization of DPPSC Versus DPMSC

Figure 17A:
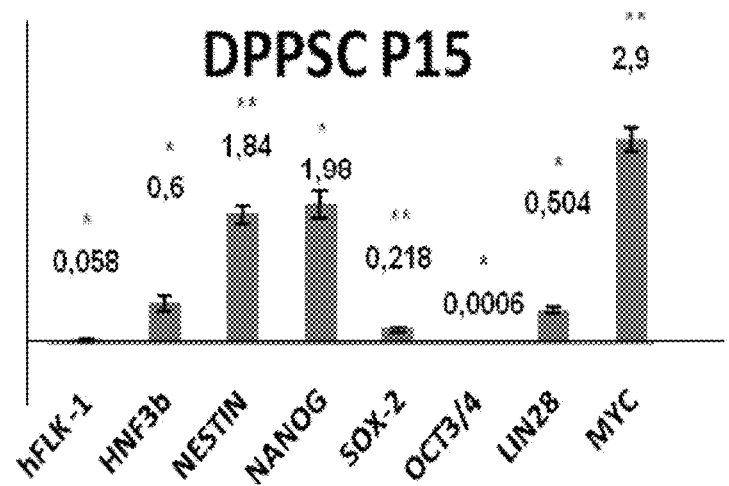
FIGS. 17A-B show the comparison of expression of different markers in DPPSC (FIG. 17A) and DPMSC (FIG. 17B) (both at P15) by Q-RT-PCR (Ntera was used as a positive control which is normalized as 1).
Figure 17B:
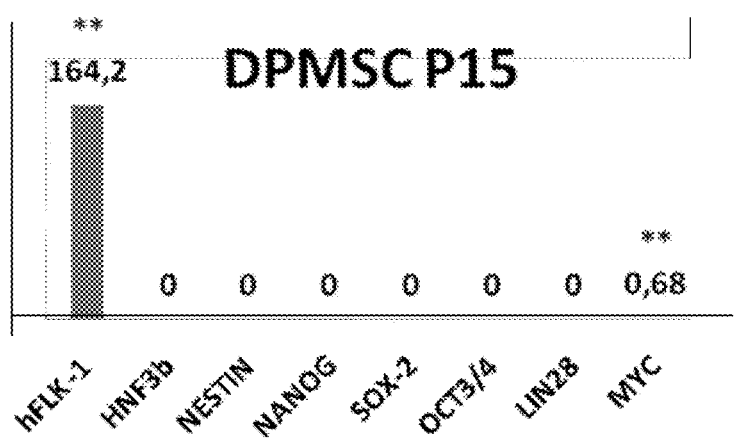

At genetic level, it was demonstrated by Q-RT-PCR that the DPPSC, in P15, express the genes of the three embryonic layers as OCT3/4+, NANOG+, hFLK-1+, HNF3beta+, Nestin+, Lin28+, Sox2+, Myc+. DPMSC have been used as negative control and Ntera cells as positive control (FIG. 17). DPMSC only express the gene hFLK-1.

Figure 18:
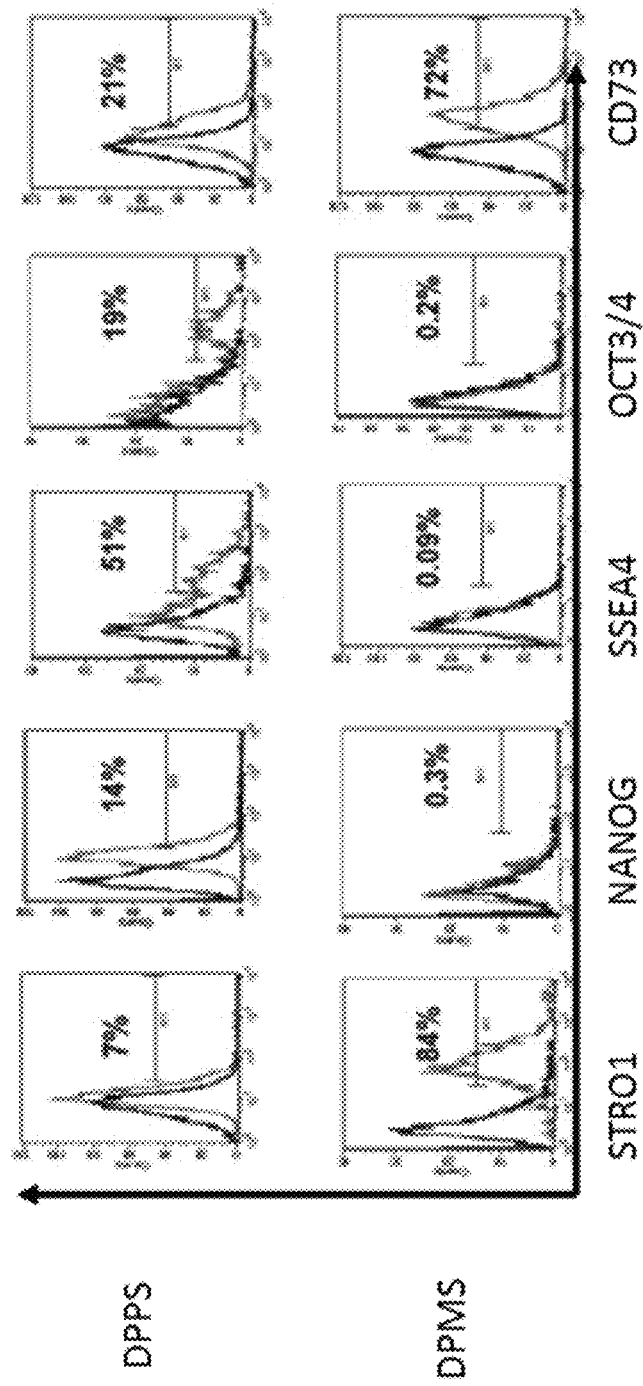
FIG. 18 shows the Immuno-phenotype by FACS analysis comparing DPPSC and DPMSC for STRO-1, NANOG, SSEA 4, OCT3/4 and CD73.

The primers used in the amplification for hFLK-1+, (SEQ ID NO 29) 5'TGGCATCGCGAAAGTGTATC3' as the forward primer, and (SEQ ID NO 30) 5'AAAGGGAGGCGAGCATCTC3' as the reverse primer. The primers used in the amplification for Myc, (SEQ ID NO 31) 5'GCGTCCTGGGAAGGGAGATCCGGAGC3' as the forward primer, and (SEQ ID NO 32) 5'TTGAGGGGCATCGTCGCGGGAGGCTG3' as the reverse primer An immunophenotype by FACS analysis comparing DPPSC and DPMSC for STRO1, NANOG, SSEA-4, OCT3/4 and CD73 was realized (FIG. 18).

Figure 19A:
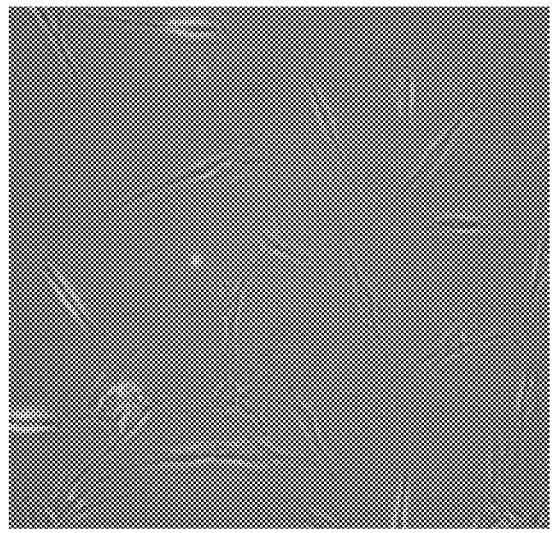
FIGS. 19A-B show cell morphology of DPMSC (FIG. 19A) and DPMSC (FIG. 19B) both at the same passage 15 (P15)
Figure 19B:
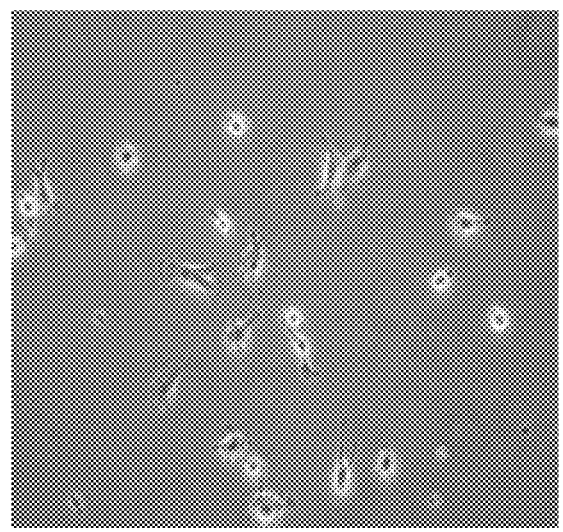

Finally the cell morphology of DPPSC and DPMSC was compare (FIG. 19).

The invention claimed is:

1. A process for obtaining a pluripotent stem cell, comprising the steps of:
   (a) disaggregating dental pulp tissue isolated from a mammal;
   (b) separating cells from the disaggregated tissue resulting from step (a);
   (c) culturing the cells in a medium comprising at least one transcription factor at a seeding concentration between 40-60 cells/cm$^2$; and
   (d) isolating a pluripotent stem cell that expresses at least the genes NANOG, SOX2, SSEA4, OCT3/4, CD105, CD13, c-Myc and CD90, and does not express the genes CD34, CD45, CD73 and CD44.

2. A culture comprising a dental pulp pluripotent stem cell that expresses at least the genes NANOG, SOX2, SSEA4, OCT3/4, CD105, CD13, c-Myc and CD90, and does not express the genes CD34, CD45, CD73 and CD44 in a culture medium comprising at least one transcription factor.

3. The culture according to claim 2, characterized in that the stem cell is a human cell.

4. The culture according to claim 2, wherein the stem cell is the stem cell with accession number DSM ACC3002 given by the institution DSMZ-Deutsche Sammlung von Mikroorganismen and Zellkulturen GmbH.

5. The culture according to claim 2, characterized in that the medium comprises at least the growth factors EGF and PDGF, and at least the transcription factor LIF.

* * * * *

```
                        SEQUENCE LISTING

<160> NUMBER OF SEQ ID NOS: 32

<210> SEQ ID NO 1
<211> LENGTH: 24
<212> TYPE: DNA
<213> ORGANISM: Artificial Sequence
<220> FEATURE:
<223> OTHER INFORMATION: forward primer glyceraldehyde 3-phosphate
      deshydrogenase (GADPH)

<400> SEQUENCE: 1
tggtatcgtg gaaggactca tgac                                            24

<210> SEQ ID NO 2
<211> LENGTH: 24
<212> TYPE: DNA
<213> ORGANISM: Artificial Sequence
<220> FEATURE:
<223> OTHER INFORMATION: reverse primer glyceraldehyde 3 phosphate
      deshydrogenase (GADPH)

<400> SEQUENCE: 2
atgccagtga gcttcccgtt cagc                                            24

<210> SEQ ID NO 3
<211> LENGTH: 26
<212> TYPE: DNA
<213> ORGANISM: Artificial Sequence
<220> FEATURE:
<223> OTHER INFORMATION: forward primer human gen SOX2

<400> SEQUENCE: 3
gggaaatggg aggggtgcaa aagagg                                          26

<210> SEQ ID NO 4
<211> LENGTH: 26
<212> TYPE: DNA
<213> ORGANISM: Artificial Sequence
<220> FEATURE:
<223> OTHER INFORMATION: reverse primer human gen SOX2

<400> SEQUENCE: 4
ttgcgtgagt gtggatggga ttggtg                                          26

<210> SEQ ID NO 5
<211> LENGTH: 20
<212> TYPE: DNA
<213> ORGANISM: Artificial Sequence
<220> FEATURE:
<223> OTHER INFORMATION: forward primer human gen NANOG

<400> SEQUENCE: 5
```
aaagaatctt cacctatgcc                                           20

<210> SEQ ID NO 6
<211> LENGTH: 20
<212> TYPE: DNA
<213> ORGANISM: Artificial Sequence
<220> FEATURE:
<223> OTHER INFORMATION: reverse primer human gen NANOG

<400> SEQUENCE: 6
gaaggaagag gagagacagt                                           20

<210> SEQ ID NO 7
<211> LENGTH: 20
<212> TYPE: DNA
<213> ORGANISM: Artificial Sequence
<220> FEATURE:
<223> OTHER INFORMATION: forward primer gen osteocalcin

<400> SEQUENCE: 7
ggtgcagagt ccagcaaagg                                           20

<210> SEQ ID NO 8
<211> LENGTH: 20
<212> TYPE: DNA
<213> ORGANISM: Artificial Sequence
<220> FEATURE:
<223> OTHER INFORMATION: reverse primer gen osteocalcin

<400> SEQUENCE: 8
agcgcctggg tctcttccta                                           20

<210> SEQ ID NO 9
<211> LENGTH: 20
<212> TYPE: DNA
<213> ORGANISM: Artificial Sequence
<220> FEATURE:
<223> OTHER INFORMATION: forward primer gen nestin

<400> SEQUENCE: 9
caggagaaac agggcctaca                                           20

<210> SEQ ID NO 10
<211> LENGTH: 20
<212> TYPE: DNA
<213> ORGANISM: Artificial Sequence
<220> FEATURE:
<223> OTHER INFORMATION: reverse primer gen nestin

<400> SEQUENCE: 10
tgggagcaaa gatccaagac                                           20

<210> SEQ ID NO 11
<211> LENGTH: 20
<212> TYPE: DNA
<213> ORGANISM: Artificial Sequence
<220> FEATURE:
<223> OTHER INFORMATION: forward primer hepatocyte nuclear factor (HNF3)

<400> SEQUENCE: 11
caggagaaac agggcctaca                                           20

<210> SEQ ID NO 12
<211> LENGTH: 20
<212> TYPE: DNA

```
<213> ORGANISM: Artificial Sequence
<220> FEATURE:
<223> OTHER INFORMATION: reverse primer gen hepatocyte nuclear factor
      (HNF3)

<400> SEQUENCE: 12
tgggagcaaa gatccaagac                                            20

<210> SEQ ID NO 13
<211> LENGTH: 20
<212> TYPE: DNA
<213> ORGANISM: Artificial Sequence
<220> FEATURE:
<223> OTHER INFORMATION: forward primer gen APHL

<400> SEQUENCE: 13
gaaggtgaag gtcggagtca                                            20

<210> SEQ ID NO 14
<211> LENGTH: 20
<212> TYPE: DNA
<213> ORGANISM: Artificial Sequence
<220> FEATURE:
<223> OTHER INFORMATION: reverse primer gen APHL

<400> SEQUENCE: 14
tggactccac gacgtactca                                            20

<210> SEQ ID NO 15
<211> LENGTH: 21
<212> TYPE: DNA
<213> ORGANISM: Artificial Sequence
<220> FEATURE:
<223> OTHER INFORMATION: forward primer gen osteonectin

<400> SEQUENCE: 15
aggtatctgt gggagctaat c                                          21

<210> SEQ ID NO 16
<211> LENGTH: 18
<212> TYPE: DNA
<213> ORGANISM: Artificial Sequence
<220> FEATURE:
<223> OTHER INFORMATION: reverse primer gen osteonectin

<400> SEQUENCE: 16
attgctgcac accttctc                                              18

<210> SEQ ID NO 17
<211> LENGTH: 20
<212> TYPE: DNA
<213> ORGANISM: Artificial Sequence
<220> FEATURE:
<223> OTHER INFORMATION: forward primer gen Tau

<400> SEQUENCE: 17
tccagtcgaa gattgggtcc                                            20

<210> SEQ ID NO 18
<211> LENGTH: 26
<212> TYPE: DNA
<213> ORGANISM: Artificial Sequence
<220> FEATURE:
<223> OTHER INFORMATION: reverse primer gen tau

<400> SEQUENCE: 18
```

```
gcttgtgggt ttcaatctttt ttatttt                                      26

<210> SEQ ID NO 19
<211> LENGTH: 22
<212> TYPE: DNA
<213> ORGANISM: Artificial Sequence
<220> FEATURE:
<223> OTHER INFORMATION: forward primer gen Nurr1

<400> SEQUENCE: 19
gctgttggga tggtcaaaga ag                                            22

<210> SEQ ID NO 20
<211> LENGTH: 18
<212> TYPE: DNA
<213> ORGANISM: Artificial Sequence
<220> FEATURE:
<223> OTHER INFORMATION: reverse primer gen nurr1

<400> SEQUENCE: 20
ggtttcgagg gcaaacga                                                 18

<210> SEQ ID NO 21
<211> LENGTH: 20
<212> TYPE: DNA
<213> ORGANISM: Artificial Sequence
<220> FEATURE:
<223> OTHER INFORMATION: forward primer hepatic nuclear factor HNF6

<400> SEQUENCE: 21
cttagcagca tgcaaaagga                                               20

<210> SEQ ID NO 22
<211> LENGTH: 20
<212> TYPE: DNA
<213> ORGANISM: Artificial Sequence
<220> FEATURE:
<223> OTHER INFORMATION: reverse primer hepatic nuclear factor HNF6

<400> SEQUENCE: 22
tgcgttcatg aagaagttgc                                               20

<210> SEQ ID NO 23
<211> LENGTH: 20
<212> TYPE: DNA
<213> ORGANISM: Artificial Sequence
<220> FEATURE:
<223> OTHER INFORMATION: forward primer hepatic nuclear factor HFN1b

<400> SEQUENCE: 23
attgctggtc gtttgttgtg                                               20

<210> SEQ ID NO 24
<211> LENGTH: 20
<212> TYPE: DNA
<213> ORGANISM: Artificial Sequence
<220> FEATURE:
<223> OTHER INFORMATION: reverse primer hepatic nuclear factor HFN1b

<400> SEQUENCE: 24
tacgtgttca tgccgttcat                                               20

<210> SEQ ID NO 25
<211> LENGTH: 20
<212> TYPE: DNA
<213> ORGANISM: Artificial Sequence
```

```
<220> FEATURE:
<223> OTHER INFORMATION: forward primer gen GATA

<400> SEQUENCE: 25
tccctcttcc ctcctcaaat                                                  20

<210> SEQ ID NO 26
<211> LENGTH: 20
<212> TYPE: DNA
<213> ORGANISM: Artificial Sequence
<220> FEATURE:
<223> OTHER INFORMATION: reverse primer gen GATA

<400> SEQUENCE: 26
ttcccctaac cagattgtcg                                                  20

<210> SEQ ID NO 27
<211> LENGTH: 24
<212> TYPE: DNA
<213> ORGANISM: Artificial Sequence
<220> FEATURE:
<223> OTHER INFORMATION: primer forward gen oct3/4

<400> SEQUENCE: 27 gacagggga ggggaggagc tagg                                              24

<210> SEQ ID NO 28
<211> LENGTH: 25
<212> TYPE: DNA
<213> ORGANISM: Artificial Sequence
<220> FEATURE:
<223> OTHER INFORMATION: reverse primer gen oct3/4

<400> SEQUENCE: 28
cttccctcca accagttgcc caaac                                            25

<210> SEQ ID NO 29
<211> LENGTH: 20
<212> TYPE: DNA
<213> ORGANISM: Artificial Sequence
<220> FEATURE:
<223> OTHER INFORMATION: forward primer gen hklf1

<400> SEQUENCE: 29
tggcatcgcg aaagtgtatc                                                  20

<210> SEQ ID NO 30
<211> LENGTH: 19
<212> TYPE: DNA
<213> ORGANISM: Artificial Sequence
<220> FEATURE:
<223> OTHER INFORMATION: reverse primer gen hklf1

<400> SEQUENCE: 30
aaagggaggc gagcatctc                                                   19

<210> SEQ ID NO 31
<211> LENGTH: 26
<212> TYPE: DNA
<213> ORGANISM: Artificial Sequence
<220> FEATURE:
<223> OTHER INFORMATION: forward primer gen Myc

<400> SEQUENCE: 31
gcgtcctggg aagggagatc cggagc                                           26
```

```
<210> SEQ ID NO 32
<211> LENGTH: 26
<212> TYPE: DNA
<213> ORGANISM: Artificial Sequence
<220> FEATURE:
<223> OTHER INFORMATION: reverse primer gen Myc

<400> SEQUENCE: 32
ttgaggggca tcgtcgcggg aggctg                                          26
```